(12) United States Patent
Imamura

(10) Patent No.: US 10,470,652 B2
(45) Date of Patent: Nov. 12, 2019

(54) INFORMATION PROCESSING APPARATUS AND INFORMATION PROCESSING METHOD

(71) Applicant: CANON KABUSHIKI KAISHA, Tokyo (JP)

(72) Inventor: Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 81 days.

(21) Appl. No.: 15/132,985

(22) Filed: Apr. 19, 2016

(65) Prior Publication Data

US 2016/0309997 A1   Oct. 27, 2016

(30) Foreign Application Priority Data

Apr. 23, 2015 (JP) ................................. 2015-088679
Dec. 22, 2015 (JP) ................................. 2015-250026

(51) Int. Cl.
*A61B 3/14* (2006.01)
*A61B 3/00* (2006.01)
*A61B 3/12* (2006.01)
*A61B 3/10* (2006.01)
*A61B 5/025* (2006.01)
(Continued)

(52) U.S. Cl.
CPC .......... *A61B 3/0025* (2013.01); *A61B 3/1025* (2013.01); *A61B 3/1241* (2013.01);
(Continued)

(58) Field of Classification Search
CPC . A61B 2017/00747; A61B 3/14; A61B 3/102; A61B 3/0025; A61B 3/1025; A61B 3/1241; A61B 5/025; A61B 8/10; A61B 2017/00769; A61B 5/024; A61F 2009/00846; A61F 2009/00865; A61F 2009/0087; A61F 2009/00872; A61F 2009/00882; A61F 2009/00887;
(Continued)

(56) References Cited

U.S. PATENT DOCUMENTS

2007/0069127 A1* 3/2007 Okuda .................... H01J 37/21
                                                                250/310
2015/0305617 A1* 10/2015 Tachikawa ............. A61B 3/102
                                                                351/206

FOREIGN PATENT DOCUMENTS

JP        2014-178474 A      9/2014

OTHER PUBLICATIONS

Yusufu N. Sulai et al.; "Visualization of retinal vascular structure and perfusion with a nonconfocal adaptive optics scanning light ophthalmoscope"; Mar. 1, 2014; J Opt Soc Am A Opt Image Sci Vis.; vol. 31, No. 3; pp. 569-579.*

(Continued)

*Primary Examiner* — Brandi N Thomas
(74) *Attorney, Agent, or Firm* — Canon U.S.A., Inc. IP Division

(57) ABSTRACT

The present invention provides a solution for focusing on each imaging target of a subject eye in a robust and highly accurate way. An information processing apparatus includes, a confocal data acquisition unit configured to acquire a confocal signal based on return light from the subject eye, a nonconfocal data acquisition unit configured to acquire a nonconfocal signal based on the return light from the subject eye, and an identification unit configured to identify an in-focus position of measurement light based at least on the nonconfocal signal out of the confocal and the nonconfocal signals.

9 Claims, 10 Drawing Sheets

(51) Int. Cl.
*G02B 26/06* (2006.01)
*A61B 5/024* (2006.01)

(52) U.S. Cl.
CPC ............ *A61B 3/14* (2013.01); *A61B 5/025* (2013.01); *G02B 26/06* (2013.01); *A61B 5/024* (2013.01)

(58) Field of Classification Search
CPC .. A61F 2009/00891; A61F 2009/00895; A61F 9/00827; A61F 9/00836; A61F 2009/00851; A61F 2009/00855; A61F 9/00806; A61F 2009/0088; G02B 21/0024; G02B 21/365; G02B 21/0028; G02B 21/0032; G02B 21/0044; G02B 21/006; G02B 21/0064; G02B 21/0068; G02B 21/0072; G02B 21/0076; G02B 21/008; G02B 21/0092; G02B 21/08; G02B 21/14; G02B 21/18; G02B 21/367; G02B 27/0068

USPC ........ 351/200, 205, 206, 209–211, 221, 222, 351/243–246
See application file for complete search history.

(56) References Cited

OTHER PUBLICATIONS

Yusufu N. Sulai et al.; "Visualization of retinal vascular structure and perfusion with a nonconfocal adaptive optics scanning light ophthalmoscope;" J. Opt. Soc. Am. A; vol. 31, No. 3; Mar. 2014; pp. 569-579.

Drew Scoles et al.; "In Vivo Imaging of Human Cone Photoreceptor Inner Segments;" The Association for Research in Vision and Ophthalmology, Inc.; IOVS ; Jul. 2014; vol. 55; No. 7; pp. 4244-4251.

* cited by examiner

FIG.3B
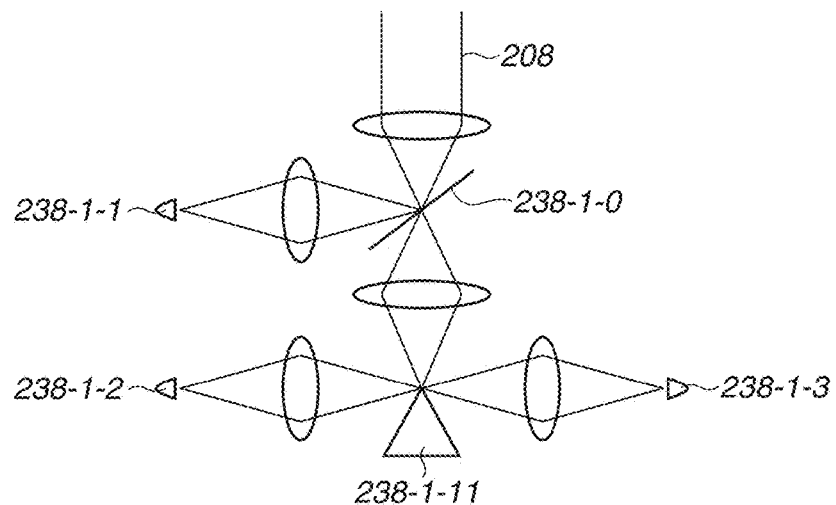
FIG.3C FIG.3D FIG.3E FIG.3F
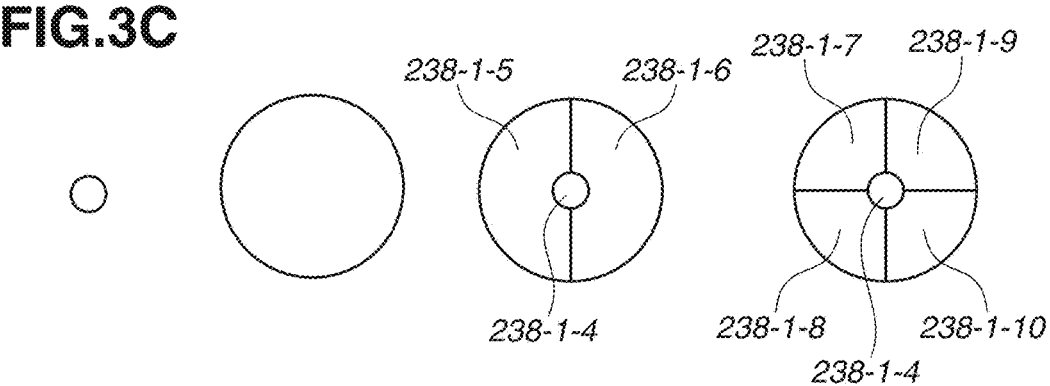

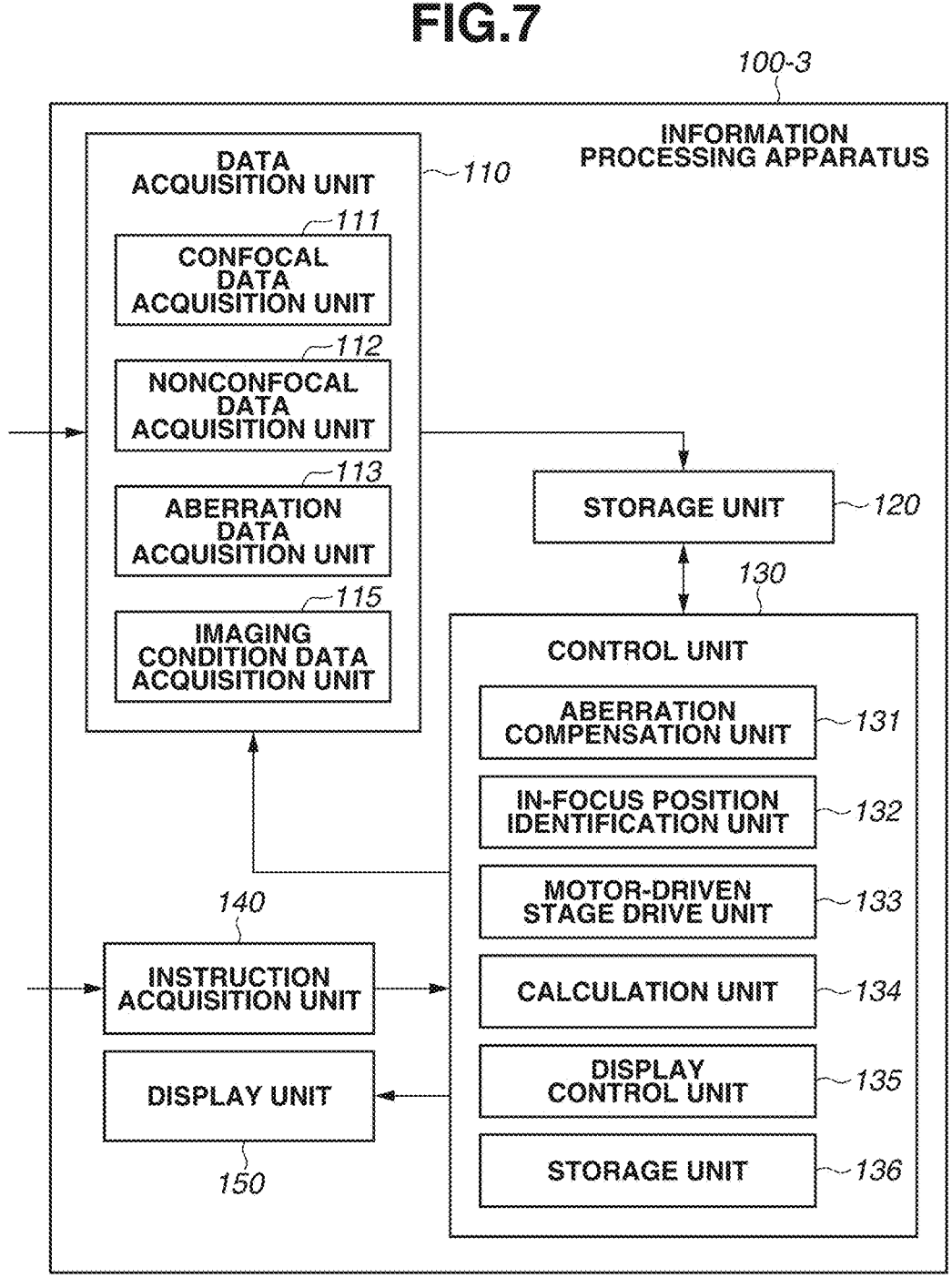

INFORMATION PROCESSING APPARATUS AND INFORMATION PROCESSING METHOD

BACKGROUND

Field

The present disclosure generally relates to an information processing apparatus and an information processing method used for ophthalmic diagnosis and treatment.

Description of the Related Art

Ocular inspections are widely performed for the purpose of preemptive medical care for lifestyle-related diseases and high ranking diseases which cause a loss of eyesight. A scanning laser ophthalmoscope (SLO), an ophthalmic apparatus based on the principle of a confocal laser scanning microscope, performs raster scanning on the fundus of a subject eye by using laser (measurement light) to obtain a planar image with a high resolution and at high speed based on the light intensity of the return light. This apparatus detects, for example, only light that has passed through the inside of an opening (pinhole) and images only return light at a specific depth position, thus acquiring a planar image having a higher contrast than an image acquired by a common fundus camera. Hereinafter, an apparatus for capturing such a planar image is referred to as an "SLO apparatus", and the captured planar image is referred to as an "SLO image."

In recent years, an SLO apparatus has become capable of acquiring an SLO image of the retina with an improved transverse resolution by increasing the beam diameter of measurement light. However, with the increase in the beam diameter of measurement light, the signal to noise (S/N) ratio and decrease of the resolution of an acquired SLO image of the retina due to the aberration of a subject eye has become problematic.

To solve this problem, there has been developed an adaptive optics SLO apparatus (AO-SLO apparatus), an SLO apparatus having an adaptive optics for measuring the aberration of a subject eye in real time by using a wave front sensor and then correcting the aberration of measurement light and the return light occurring in the subject eye with a wave front correction device.

This adaptive optics SLO apparatus enables acquiring an SLO image having a high transverse resolution. Further, the adaptive optics SLO apparatus is capable of acquiring such an SLO image having a high transverse resolution as a moving image. Therefore, for example, to noninvasively observe the hemodynamics, the adaptive optics SLO apparatus is further capable of extracting the retinal blood vessels from each frame and measuring the moving speed of blood cells in the capillary vessels. When observing the visual cells, the adaptive optics SLO apparatus captures an SLO image by setting an in-focus position in the vicinity of the retina outer layers.

Furthermore, to evaluate the relation between the visual performance and the photoreceptor cells of the subject eye by using an SLO image, the adaptive optics SLO apparatus detects photoreceptor cells P illustrated in FIG. 6B and then measures the density distribution and the arrangement of the visual cells P. FIG. 6B illustrates an example of an SLO image with a high transverse resolution. The photoreceptor cells P, a low-luminance region Q corresponding to the capillary vessel position, and a high-luminance region W corresponding to the white corpuscle position can be observed from the SLO image illustrated in FIG. 6B. When observing the photoreceptor cells P, the adaptive optics SLO apparatus sets an in-focus position in the vicinity of the retina outer layer B5 illustrated in FIG. 6A and then captures an SLO image as illustrated in FIG. 6B. Meanwhile, retinal blood vessels and branched capillary vessels run in the retina inner layers B2 to B4 illustrated in FIG. 6A. When an in-focus position is set in the retina inner layers and an SLO image is captured by using the adaptive optics SLO apparatus, it becomes possible to directly observe, for example, the retinal blood vessel walls which are microstructures related to the retinal blood vessels.

However, in a confocal image of the retina inner layers in the SLO image, the observation of the blood vessel walls and the detection of wall boundaries may be difficult because of intense noise signals under the influence of reflected light from the nerve fiber layer. In recent years, there has been used a method for observing a nonconfocal image obtained by acquiring dispersion light by changing the diameter, the shape, and the position of a pinhole provided before an optical sensor (for example, refer to Non-Patent Document 1 (described below)). In a nonconfocal image in the SLO image, it is easy to observe an object having irregularities in the depth direction such as blood vessels because of a large depth of focus. Further, since reflected light direct from the nerve fiber layer is not easily received, noise can be reduced.

In addition, when observing the photoreceptor cells in the retina outer layers, conventionally in the confocal image, mainly the photoreceptor outer segment is captured. Whereas it has been known that in the nonconfocal image, an image of irregularities of the photoreceptor inner segment (for example, refer to Non-Patent Document 2 (described below)) is captured. A region of the visual cells where the photoreceptor outer segment is lost due to initial lesion, however, the photoreceptor inner segment exists is differently observed between the confocal image and the nonconfocal image. In the confocal image, the relevant region is observed as a black missing region (see FIG. 6G). In the nonconfocal image, the relevant region is observed as a region where high-luminance granular objects exist (see FIG. 6H).

Non-Patent Document 1 discusses a technique for acquiring the nonconfocal image of the retinal blood vessels by using an adaptive optics SLO apparatus. Further, Non-Patent Document 2 discusses a technique for simultaneously acquiring the confocal image and the nonconfocal image by using an adaptive optics SLO apparatus. Japanese Patent Application Laid-Open No. 2014-178474 discusses a technique used when capturing an image of a preparation that holds a sample by using a microscope. The technique calculates a provisional in-focus position of an object lens included in a first optical system based on an image acquired through a second optical system having a depth of field larger than the first optical system. Then, an in-focus position of the object lens based on the provisional in-focus position and an image acquired through the first optical system are searched for.

NON-PATENT DOCUMENTS

[Non-Patent Document 1] Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014.

[Non-Patent Document 2] Scoles, Dubra et al.; "In vivo Imaging of Human Cone Photoreceptor Inner Segment", IOVS, Vol. 55, No. 7, pp. 4244-4251, 2014.

In an SLO apparatus for acquiring a plurality of image types including a confocal image of a subject eye, it is common to determine an in-focus position of the subject eye based only on the confocal image. However, a problem arises when it is attempted to focus on the retinal blood vessels (or the retina outer layers where the photoreceptor cells are lost) based only on the confocal image (such photoreceptor cells are observed as a low-luminance region in the confocal image). In that case, it is difficult to determine an optimum in-focus position due to much noise by reflected light from the nerve fiber layer (or due to a low amount of reflected light from the photoreceptor cell layer).

The techniques discussed in Non-Patent Document 1, Non-Patent Document 2, and Japanese Patent Application Laid-Open No. 2014-178474 have not solved the above-described problem. More specifically, in a case of an imaging target which is difficult to focus on if in a confocal image (a confocal signal according to a broader concept), such as the retinal blood vessels and the retina outer layers where the photoreceptor cells of the subject eye are lost, the conventional techniques have a problem in that it is difficult to focus on the target in a robust and highly accurate way.

SUMMARY OF THE INVENTION

The present invention is directed to providing a solution for focusing on each imaging target of a subject eye in a robust and highly accurate way.

According to an aspect of the present invention, an information processing apparatus includes, an acquisition unit configured to acquire a confocal signal and a nonconfocal signal based on return light from a subject eye irradiated with measurement light, and an identification unit configured to identify an in-focus position of the measurement light based at least on the nonconfocal signal out of the confocal and the nonconfocal signals.

According to another aspect of the present invention, the present invention includes an information processing method performed by the above-described information processing apparatus.

Further features of the present invention will become apparent from the following description of exemplary embodiments with reference to the attached drawings.

BRIEF DESCRIPTION OF THE DRAWINGS

FIGS. 3B to 3F schematically illustrate an example of a configuration of a light receiving unit in FIG. 3A.

FIG. 7 is a block diagram illustrating an example of a functional configuration of the information processing apparatus in FIG. 1B according to the third exemplary embodiment of the present invention.

DESCRIPTION OF THE EMBODIMENTS

Desirable exemplary embodiments of an information processing apparatus and an information processing method according to the present invention will be described below with reference to the accompanying drawings.

An information processing apparatus according to a first exemplary embodiment identifies an approximate in-focus position by adding normal value data related to a predetermined retinal shape to a position focused using a confocal signal at the time of aberration compensation, and then identifies an accurate, detailed in-focus position for the retinal blood vessels based at least on a nonconfocal signal. In the following descriptions, the confocal signal is equivalent to the broader concept of a confocal image including the confocal image. The confocal signal is not limited to two-dimensional information such as a confocal image, and may be, for example, one-dimensional information. Likewise, the nonconfocal signal is equivalent to the broader concept of a nonconfocal image including the nonconfocal image. The nonconfocal signal is not limited to two-dimensional information such as a nonconfocal image, and may be, for example, one-dimensional information.

The reason why it is desirable to use the nonconfocal signal instead of the confocal signal in identifying a detailed in-focus position for the blood vessel of the retina inner layers, is that the nonconfocal signal is more immune to noise effects caused by reflected light from the nerve fiber layer, and hence makes it easier to determine an optimum in-focus position than the confocal signal.

In the following descriptions of the present exemplary embodiment, when capturing an image of the retinal blood vessels of a subject eye by using an apparatus for acquiring a confocal signal and a nonconfocal signal of the subject eye at almost the same time, the apparatus identifies an approximate in-focus position by adding normal value data related to the distance between the photoreceptor cells and the retinal blood vessels to the in-focus position at the time of aberration compensation. Thus, an accurate, detailed in-focus position for the retinal blood vessels is identified based on the approximate in-focus position and the nonconfocal signal.

(Overall Configuration of Information Processing System)

Figure 1A:
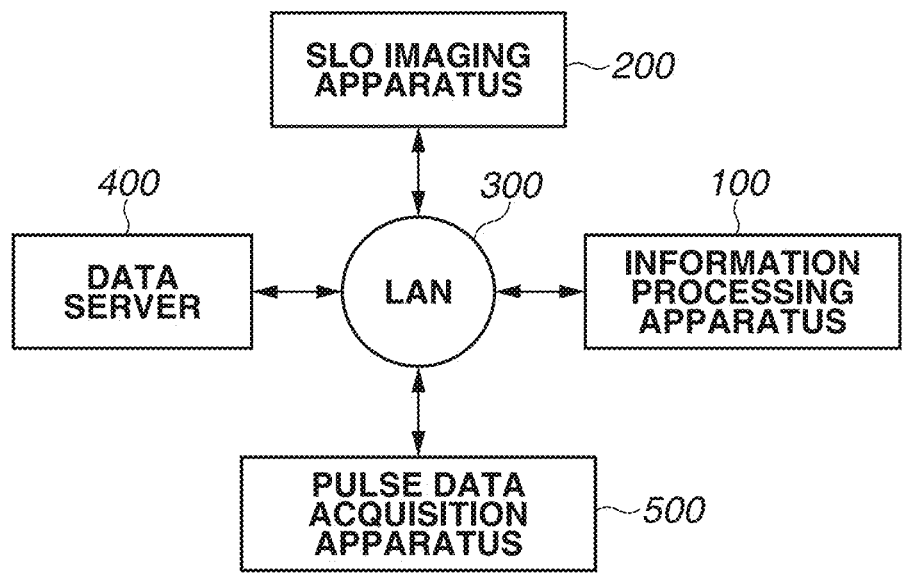
FIG. 1A illustrates an example of an overall configuration of an information processing system including an information processing apparatus according to a first exemplary embodiment of the present invention.

FIG. 1A illustrates an example of an overall configuration of an information processing system 10-1 including an information processing apparatus 100 according to the first exemplary embodiment of the present invention. As illustrated in FIG. 1A, the information processing system 10-1 includes the information processing apparatus 100, an SLO image capturing apparatus 200, a local area network (LAN) 300, a data server 400, and a pulse data acquisition apparatus 500.

As illustrated in FIG. 1A, the information processing apparatus 100 is communicably connected with the SLO image capturing apparatus 200, the data server 400, and the pulse data acquisition apparatus 500 via the LAN 300. The information processing apparatus 100 may be connected with the SLO image capturing apparatus 200, the data server 400, and the pulse data acquisition apparatus 500 via an external network such as the Internet, or may be directly connected with these apparatuses.

The SLO image capturing apparatus 200 is an apparatus for capturing a wide viewing angle image Dl, a confocal image Dc, and a nonconfocal image Dn of the subject eye. The confocal image Dc and the nonconfocal image Dn are images captured with higher magnifications than the wide viewing angle image Dl. The SLO image capturing apparatus 200 transmits the wide viewing angle image Dl, the confocal image Dc, the nonconfocal image Dn, and information about fixation target positions Fl and Fcn used when capturing these images, to the information processing apparatus 100 and the data server 400.

The pulse data acquisition apparatus 500 is an apparatus for acquiring autonomously changing biological signal data (pulse data) of the subject. The pulse data acquisition apparatus 500 includes a sphygmograph or an electrocardiograph. In response to an operation by the subject, the pulse data acquisition apparatus 500 acquires the above-described wide viewing angle image Dl, confocal image Dc, and nonconfocal image Dn, and at the same time acquires pulse data Pi. Then, the pulse data acquisition apparatus 500 transmits the acquired pulse data Pi to the information processing apparatus 100 and the data server 400. The pulse data acquisition apparatus 500 may be directly connected to the SLO image capturing apparatus 200.

In the following descriptions, in a case of acquiring the wide viewing angle image Dl, the confocal image Dc, and the nonconfocal image Dn at different imaging positions, these images are referred to as wide viewing angle images Dli, confocal images Dcj, and nonconfocal images Dnk, respectively, where i, j, and k are variables indicating imaging position numbers (i=1, 2, ..., imax, j=1, 2, ..., jmax, and k=1, 2, ..., kmax). Further, in a case of acquiring the confocal image Dc and the nonconfocal image Dn with different magnifications, these images are described in descending order of magnification (starting with the image with the highest magnification), for example, Dc1$m$, Dc2$o$, ... (in case of the confocal image Dc), and Dn1$m$, Dn2$o$, ... (in case of the nonconfocal image Dn). The confocal image Dc1$m$ is referred to as a high-magnification confocal image, and the confocal image Dc2$o$ and subsequent images are referred to as intermediate-magnification confocal images. Likewise, a nonconfocal image Dn1$m$ is referred to as a high-magnification nonconfocal image, and the nonconfocal image Dn2$o$ and subsequent images are referred to as intermediate-magnification nonconfocal images.

The data server 400 stores the wide viewing angle image Dl, the confocal image Dc, and the nonconfocal image Dn of the subject eye, imaging condition data such as the fixation target positions Fl and Fcn, and the in-focus position used for imaging, the pulse data Pi, and the normal value data related to image features of the subject eye. As normal value data related to image features of the subject eye, the present exemplary embodiment applies the normal value of the distance between the photoreceptor cells P and the retinal blood vessels at each position on the fundus of the subject eye. In response to a request from the information processing apparatus 100, the data server 400 transmits the wide viewing angle image Dl, the confocal image Dc, the nonconfocal image Dn, the pulse data Pi, and the imaging condition data such as the fixation target positions Fl and Fcn and the in-focus position, to the information processing apparatus 100.

The LAN 300 connects the information processing apparatus 100, the SLO image capturing apparatus 200, the data server 400, and the pulse data acquisition apparatus 500 to enable communication therebetween. For example, the LAN 300 includes optical fibers, universal serial bus (USB) cables, and Institute of Electrical and Electronics Engineers (IEEE) 1394 cables.

<Functional Configuration of Information Processing Apparatus>

Figure 2:
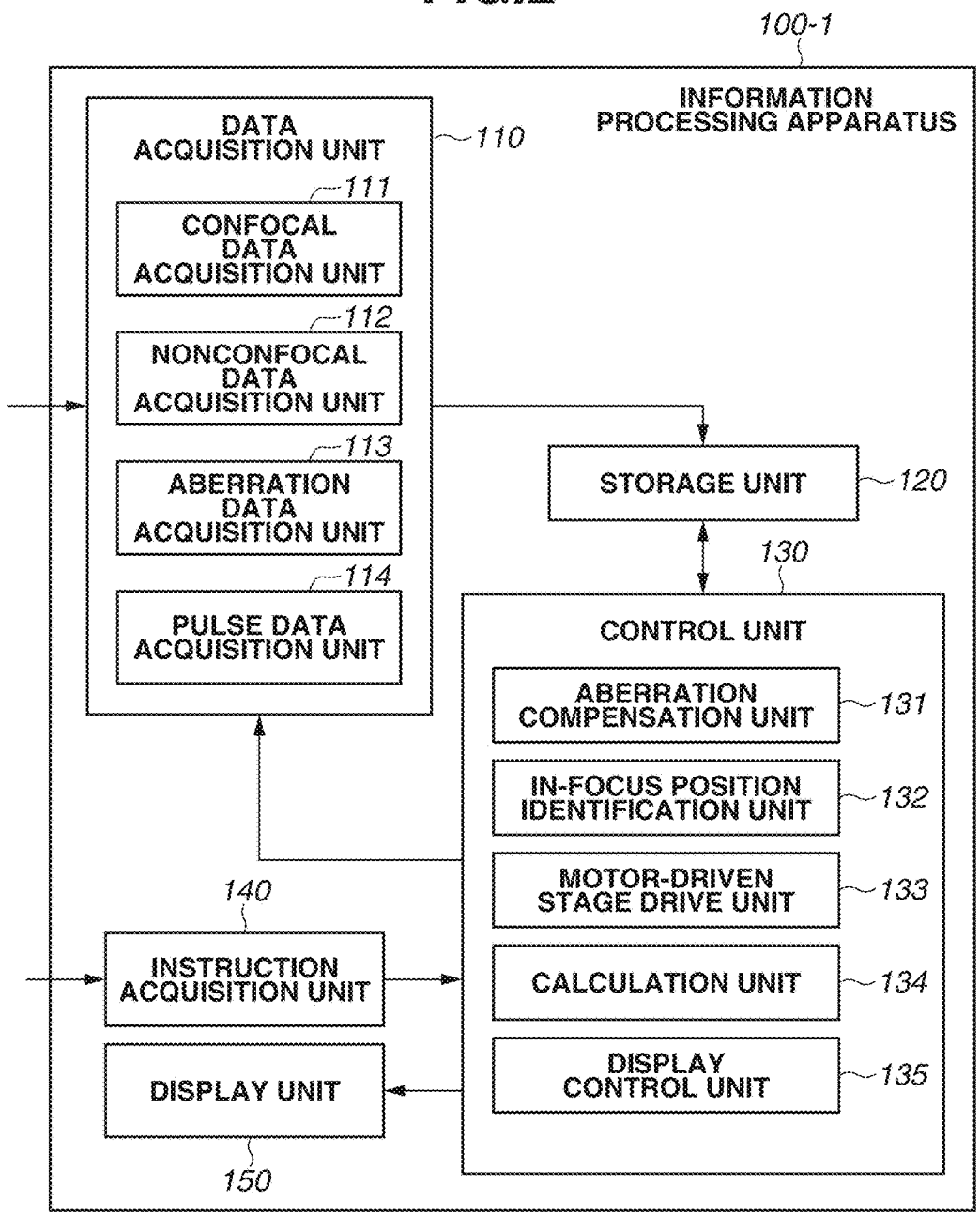
FIG. 2 is a block diagram illustrating an example of a functional configuration of the information processing apparatus illustrated in FIG. 1A according to the first exemplary embodiment of the present invention.

FIG. 2 is a block diagram illustrating an example of a functional configuration of the information processing apparatus 100 illustrated in FIG. 1A according to the first exemplary embodiment of the present invention. Referring to FIG. 2, the information processing apparatus 100 according to the first exemplary embodiment is described as an "information processing apparatus 100-1."

As illustrated in FIG. 2, the information processing apparatus 100-1 includes a data acquisition unit 110, a storage unit 120, a control unit 130, an instruction acquisition unit 140, and a display unit 150.

The data acquisition unit 110 acquires various types of data, for example, from the SLO image capturing apparatus 200, the data server 400, and the pulse data acquisition apparatus 500 illustrated in FIG. 1A. As illustrated in FIG. 2, the data acquisition unit 110 includes a confocal data acquisition unit 111, a nonconfocal data acquisition unit 112, an aberration data acquisition unit 113, and a pulse data acquisition unit 114. The internal configuration of the data acquisition unit 110 will be described below, together with the flowcharts illustrated in FIGS. 5A to 5C.

The storage unit 120 stores various types of data and various types of information.

The control unit 130 totally controls operations of the information processing apparatus 100-1. As illustrated in FIG. 2, the control unit 130 includes an aberration compensation unit 131, an in-focus position identification unit 132, a motor-driven stage drive unit 133, a calculation unit 134, and a display control unit 135. The internal configuration of the control unit 130 will be described below, together with the flowcharts illustrated in FIGS. 5A to 5C.

The instruction acquisition unit 140 acquires an instruction, for example, input from an inspector and then outputs the instruction to the control unit 130.

The display unit 150 displays various types of images and various types of information under the control of the control unit 130 (more specifically, the display control unit 135).

<Overall Configuration of SLO Image Capturing Apparatus>

Figure 3A:
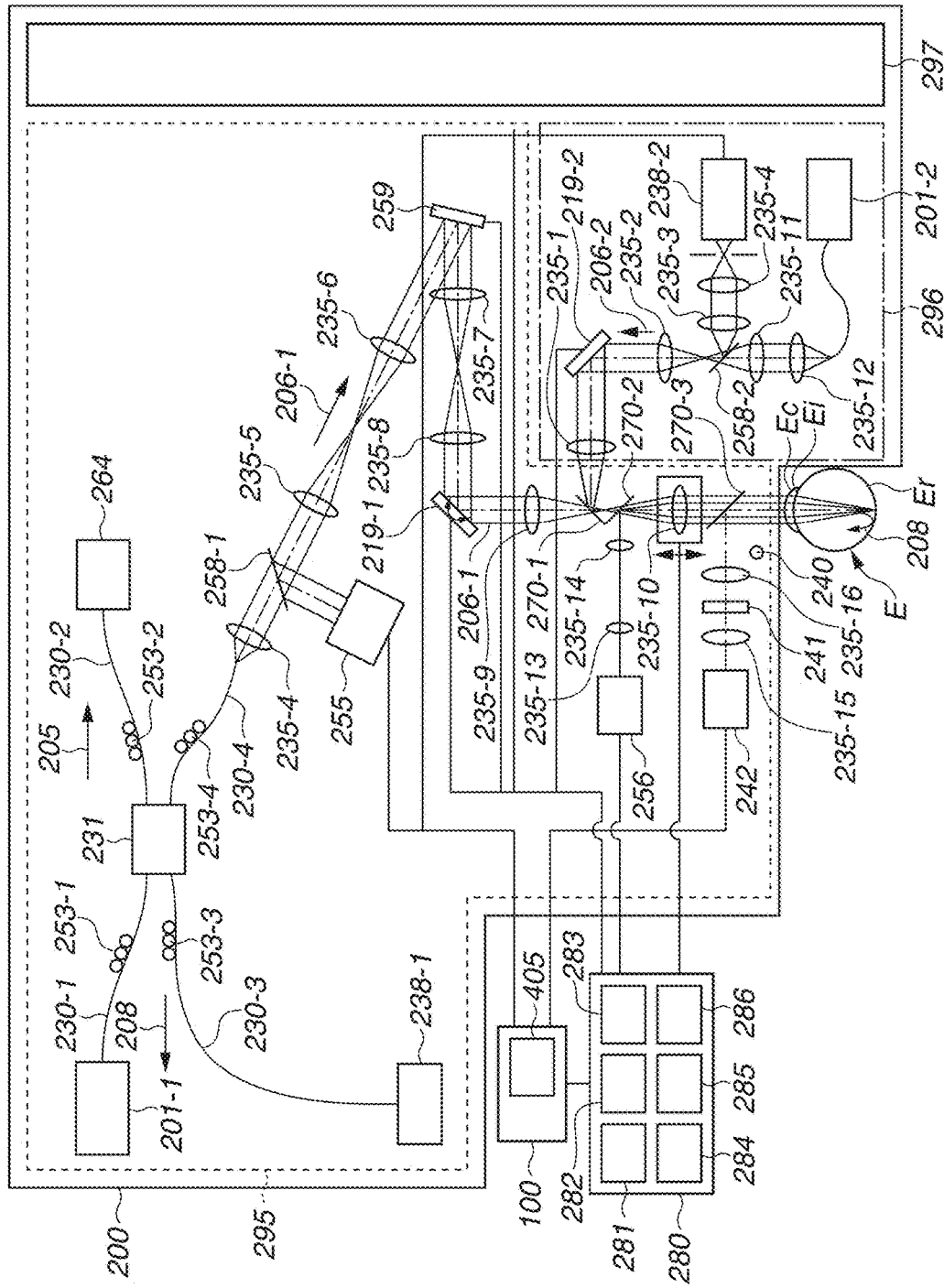
FIG. 3A illustrates an example of an overall configuration of a scanning laser ophthalmoscope (SLO) image capturing apparatus illustrated in FIGS. 1A and 1B.

FIG. 3A illustrates an example of an overall configuration of the SLO image capturing apparatus 200 illustrated in FIG. 1A. Referring to FIG. 3A, elements identical to those in the configuration illustrated in FIG. 1A are assigned the same reference numeral. FIG. 3A illustrates a driver unit 280 for the information processing apparatus 100 managing the drive control for the SLO image capturing apparatus 200.

The SLO image capturing apparatus 200 includes an adaptive optics SLO unit 295, a wide viewing angle SLO unit 296, and an apparatus body motor-driven stage unit 297. The adaptive optics SLO unit 295 acquires the confocal image Dc and the nonconfocal image Dn which are high-magnification images of a subject eye E under the control of the information processing apparatus 100. The wide viewing angle SLO unit 296 acquires the wide viewing angle image Dl aiming for assisting the acquisition of the confocal image Dc and the nonconfocal image Dn which are high-magnification images under the control of the information processing apparatus 100. The apparatus body motor-driven stage unit 297 electrically aligns the adaptive optics SLO unit 295 and the wide viewing angle SLO unit 296 for the subject eye E under the control of the information processing apparatus 100.

<<Adaptive Optics SLO Unit>>

The adaptive optics SLO unit 295 illustrated in FIG. 3A will be described below.

The overall configuration of the adaptive optics SLO unit 295 will be described below.

Light emitted from the light source 201-1 is split into reference light 205 and measurement light 206-1 by an optical coupler 231. The measurement light 206-1 is led to the subject eye E as an observation target (inspection target) via a single mode optical fiber 230-4, a spatial light modulator 259, an XY scanner 219-1, and a dichroic mirror 270-2. A light flux (not illustrated) from a fixation light indicator 256 has a role of prompting the fixation of the subject eye E.

An anterior ocular segment illumination light source 240 including an infrared light emitting diode (LED) for emitting infrared light to observe the anterior ocular segment of the subject eye E is disposed in the vicinity of the subject eye E. An image in the vicinity of the iris Ei based on light which illuminates the anterior ocular segment of the subject eye E is captured by an anterior ocular segment observation camera 242 via a dichroic mirror 270-3, a lens 235-16, a split prism 241, and a lens 235-15.

The measurement light 206-1 has been reflected or scattered by the subject eye E and becomes return light 208 which backwardly advances in the light path and then enters a light receiving unit 238-1 via the optical coupler 231. The light receiving unit 238-1 converts the light intensity of the return light 208 into a voltage signal, which is used to form a planar image of the subject eye E.

Although, in the example illustrated in FIG. 3A, the entire optical system is composed mainly of a refractive optical system using lenses, the entire optical system composed of a reflective optical system using spherical mirrors instead of lenses is also applicable to the present exemplary embodiment. Although, in the example illustrated in FIG. 3A, the reflective spatial light modulator 259 is used as an aberration compensation device, the use of a transmissive spatial light modulator and a variable shape mirror is also applicable to the present exemplary embodiment.

The periphery of the light source 201-1 will be described below.

The light source 201-1 is, for example, a super luminescent diode (SLD) which is a typical low-coherent light source. The wavelength of the light emitted from the light source 201-1 is about 830 nanometers and the bandwidth thereof is about 50 nanometers. As the light source 201-1, a low-coherent light source is selected to acquire an SLO image having little speckle noise. Although an SLD is selected as a type of the light source 201-1, it is also possible to use, for example, an amplified spontaneous emission (ASE) since the light source 201-1 only needs to emit low-coherent light. In terms of the measurement of the subject eye E, near-infrared light is suitable as the light emitted from the light source 201-1. Further, since the wavelength of the light emitted from the light source 201-1 affects the transverse resolution of an SLO image to be acquired, the wavelength of the light is desirably as short as possible and hence is set to about 830 nanometers. Other wavelengths may be selected depending on the measurement portion of an observation target. The light emitted from the light source 201-1 is split into the reference light 205 and the measurement light 206-1, for example, with a ratio of 96:4 via a single mode optical fiber 230-1 and the optical coupler 231. The optical fibers 230-1 to 230-4 are provided with polarization controllers 253-1 to 253-4, respectively.

The optical path of the reference light 205 will be described below.

The reference light 205 split by the optical coupler 231 enters a light quantity measuring device 264 via the optical fiber 230-2. The light quantity measuring device 264 is used for monitoring the light quantity of the measurement light 206-1 by measuring the light quantity of the reference light 205.

The optical path of the measurement light 206-1 will be described below.

The measurement light 206-1 split by the optical coupler 231 is led to the lens 235-4 via the single mode optical fiber 230-4 to be adjusted to become parallel light having a beam diameter of about 4 millimeters. The measurement light 206-1 passes through a beam splitter 258-1 and lenses 235-5 to 235-6, and then enters the spatial light modulator 259. The spatial light modulator 259 is controlled by the information processing apparatus 100 via a spatial light modulator driver 281 in the driver unit 280. Subsequently, the measurement light 206-1 is modulated by the spatial light modulator 259, passes through the lenses 235-7 to 235-8, and then enters the mirror of the XY scanner 219-1. Although the XY scanner 219-1 is illustrated as one mirror in FIG. 3A for simplification, the XY scanner 219-1 actually includes two mirrors of an X scanner and a Y scanner adjacently disposed, and performs raster scanning on the fundus Er in the direction perpendicular to the optical axis. The center of the measurement light 206-1 is adjusted to coincide with the rotation center of the mirror of the XY scanner 219-1.

The X scanner, a component of the XY scanner 219-1, scans with the measurement light 206-1 in the direction parallel to paper. A resonant scanner is used as the X scanner in the exemplary embodiment. The drive frequency of the X scanner is about 7.9 kHz. The Y scanner, a component of the XY scanner 219-1, scans with the measurement light 206-1 in the direction perpendicular to paper. A Galvano scanner is used as the Y scanner in the exemplary embodiment. The drive waveform of the Y scanner is a sawtooth form of which the drive frequency is about 64 Hz and the duty ratio is about 81%. The drive frequency of the Y scanner is an important parameter which determines the frame rate of the above-described high-magnification images to be captured by the adaptive optics SLO unit 295. The XY scanner 219-1 is controlled by the information processing apparatus 100 via an optical scanner driver 282 in the driver unit 280.

Lenses 235-9 to 235-10 form an optical system having a role in scanning the fundus Er with the measurement light 206-1 by using a point in the vicinity of the iris Ei as a fulcrum. Although, in the present exemplary embodiment, the beam diameter of the measurement light 206-1 is about 4 mm, the beam diameter may be increased to acquire images with higher resolutions. An motor-driven stage 217 can be moved in a direction indicated by the arrow to adjust the position of the accompanying lens 235-10. The motor-driven stage 217 is controlled by the information processing apparatus 100 via a motor-driven stage driver 283 in the driver unit 280.

By adjusting the position of the lens 235-10, the light 206-1 can be adjusted in a predetermined layer of the fundus Er of the subject eye E to allow observation of the relevant layer. This adjustment also enables addressing a case where the subject eye E shows abnormal refraction.

When the measurement light 206-1 enters the subject eye E, the return light 208 produced by reflection and dispersion from the fundus Er is led to the optical coupler 231, and reaches the light receiving unit 238-1 via a single mode optical fiber 230-3. The light receiving unit 238-1 includes, for example, an avalanche photo diode (APD) or a photo-multiplier tube (PMT) which is high-speed, high-sensitivity optical sensors. An APD is used as an optical sensor in the exemplary embodiment.

The return light 208 is re-modulated by the spatial light modulator 259. A part of the return light 208 split by the beam splitter 258-1 enters a wave front sensor 255 which measures the aberration of the return light 208 which occurs in the subject eye E. The wave front sensor 255 is electrically connected to the information processing apparatus 100.

The lenses 235-5 to 235-10 are disposed so that the iris Ei, the XY scanner 219-1, the wave front sensor 255, and the spatial light modulator 259 become optically conjugate. Therefore, the wave front sensor 255 enables measurement of the aberration of the subject eye E. The spatial light modulator 259 enables compensation of the aberration of the subject eye E. In addition, based on the aberration acquired from the result of the measurement by the wave front sensor 255, the information processing apparatus 100 controls the spatial light modulator 259 in real time to enable the compensation of the aberration occurring in the subject eye E and SLO images can be acquired with higher resolutions. Although the lens 235-10 is a spherical lens, a cylindrical lens may be used instead of a spherical lens depending on the aberration (abnormal refraction) of the subject eye E. Further, an optional lens may be added to the optical path of the measurement light 206-1. Although aberration is measured by using the measurement light 206-1 and the wave front sensor 255, other light sources may be used for aberration measurement. Further, other optical paths may be configured for aberration measurement. For example, it is also possible to cause light for aberration measurement to enter from between the lens 235-10 and the dichroic mirrors 270-3 by using another beam splitter.

The fixation light indicator 256 includes an active type display module, and has a display surface (27 square millimeters, 128 pixels by 128 pixels) in the yz plane. For example, a liquid crystal, an organic electroluminescence (EL), an LED array, etc. can be used as the fixation light indicator 256. By making the subject eye E gaze at a light flux from the fixation light indicator 256, the fixation of the subject eye E is prompted. A blinking cross pattern is displayed at an arbitrary lighting position on the display surface of the fixation light indicator 256. The light flux from the fixation light indicator 256 is led to the fundus Er via lenses 235-13 to 235-14, the dichroic mirror 270-2, and the lens 235-10. The lenses 235-10, 235-13, and 235-14 are disposed so that the display surface of the fixation light indicator 256 and the fundus Er become optically conjugate. The fixation light indicator 256 is controlled by the information processing apparatus 100 via a fixation light driver 284 in the driver unit 280.

The configuration of a measurement system of the adaptive optics SLO unit 295 will be described below.

The adaptive optics SLO unit 295 is capable of acquiring an adaptive optics SLO image composed of the light intensity of the return light 208 from the fundus Er. The return light 208, which is the light reflected and scattered by the fundus Er, enters the light receiving unit 238-1 via the lenses 235-4 to 235-10, the spatial light modulator 259, and the optical coupler 231. The light intensity is converted into a voltage signal by the light receiving unit 238-1. The voltage signal acquired by the light receiving unit 238-1 is converted into a digital value by an analog-to-digital (AD) board 405 in the information processing apparatus 100. The information processing apparatus 100 performs data processing on the digital signal in synchronization with the operation and drive frequency of the XY scanner 219-1 to form an SLO image. The sampling rate of the AD board 405 is, for example, about 15 MHz. A part of the return light 208 split by the beam splitter 258-1 enters the wave front sensor 255 which measures the aberration of the return light 208. The wave front sensor 255 is, for example, a Shack-Haltman wave front sensor, and has a narrow measurement range from −1D to +1D (D: diopter) and high measurement accuracy. The acquired aberration is represented, for example, by using the Zernike polynomials, and indicates the aberration of the subject eye E. The Zernike polynomials include the tilt (inclination) term, the defocus term, the astigmatism term, the coma term, the trefoil term, and so on.

An overall configuration of the light receiving unit 238-1 will be described below.

FIG. 3B illustrates an example of an overall configuration of the light receiving unit 238-1 illustrated in FIG. 3A. Referring to FIG. 3B, the return light 208 enters a light shielding unit 238-1-0 disposed on the image-forming surface. A part of the return light 208 that entered the light shielding unit 238-1-0 is reflected off the light shielding unit 238-1-0 and then enters an optical sensor 238-1-1.

The light shielding unit 238-1-0 illustrated in FIG. 3B will be described below.

As illustrated in FIG. 3E, for example, the light shielding unit 238-1-0 is composed of transmissive areas 238-1-5 and 238-1-6, a light-shielded area between the transmissive areas 238-1-5 and 238-1-6, and a reflective area 238-1-4. The light shielding unit 238-1-0 is disposed such that its center is positioned at the center of the optical axis of the return light 208. The light shielding unit 238-1-0 has such an elliptical shaped pattern that, when obliquely disposed with respect to the optical axis of the return light 208, takes a round shape when viewed from the optical axis.

As described above, a part of the return light 208 that has entered the light shielding unit 238-1-0 is reflected off the light shielding unit 238-1-0 and then enters the optical sensor 238-1-1. A part of the return light 208 that has entered the light shielding unit 238-1-0, i.e., light that has passed through the transmissive areas 238-1-5 and 238-1-6 of the light shielding unit 238-1-0 is split by a prism 238-1-11 disposed on the image-forming surface and then enters the optical sensors 238-1-2 and 238-1-3, respectively, as illustrated in FIG. 3B. The optical sensors 238-1-2 and 238-1-3 are coaxially disposed with scanning directions of the XY scanner 219-1.

The voltage signals acquired by the optical sensors 238-1-1 to 238-1-3 are converted into digital values by the AD board 405 in the information processing apparatus 100, and then is further converted into an image signal by the information processing apparatus 100. The image signal of the subject eye E acquired based on the light that has entered the optical sensor 238-1-1 becomes a confocal image (a confocal signal according to the broader concept) focused on a specific narrow range. Further, the image signal of the subject eye E acquired based on the light that has entered the optical sensors 238-1-2 and 238-1-3 becomes a nonconfocal image (a nonconfocal signal according to the broader concept) focused on a broad range.

The method for splitting light to acquire a nonconfocal signal is not limited to the method using the light shielding unit 238-1-0 illustrated in FIG. 3E. For example, as illustrated in FIG. 3F, it is also possible to apply a method for splitting light into four by using the light shielding unit 238-1-0 having four transmissive areas 238-1-7, 238-1-8, 238-1-9, and 238-1-10 to acquire a nonconfocal signal.

Further, the method for receiving a confocal signal and a nonconfocal signal is not limited to the method illustrated in FIG. 3B. For example, with one optical sensor provided inside the light receiving unit 238-1 and an opening (pinhole) disposed before the optical sensor, a confocal signal and a nonconfocal signal may be received by the optical sensor by adjusting the diameter, position, and shape of the opening. In this case, for example, a confocal signal may be received by the optical sensor by decreasing the diameter of the opening as illustrated in FIG. 3C, or a nonconfocal signal may be received by the optical sensor by increasing the diameter of the opening as illustrated in FIG. 3D. In this case, the diameter and the moving amount of the opening can be arbitrarily set. More specifically, for example, referring to FIG. 3C, the diameter of the opening is set to about 1 Airy Disc Diameter (ADD). Referring to FIG. 3D, the diameter of the opening is set to about 10 ADD, and the moving amount is set to about 6 ADD.

In the present exemplary embodiment, since the light receiving unit 238-1 illustrated in FIG. 3B is applied (the structure of the light shielding unit 238-1-0 in FIG. 3B is illustrated in FIG. 3E), there are two types of nonconfocal signals. Therefore, one type of nonconfocal signal is referred to as Dnr which means an R channel image, and the other type of nonconfocal signal is referred to as Dnl which means an L channel image. A nonconfocal image Dn indicates both a nonconfocal image Dnr (R channel image) and a nonconfocal image Dnl (L channel image).

<<Wide Viewing Angle SLO Unit>>

The wide viewing angle SLO unit 296 illustrated in FIG. 3A will be described below.

The wide viewing angle SLO unit 296 basically has a similar configuration to that of the adaptive optics SLO unit 295 except that the wide viewing angle SLO unit 296 does not include an adaptive optics and a reference optical path. In the following descriptions, descriptions of portions identical with the adaptive optics SLO unit 295 will be omitted.

The overall configuration of the wide viewing angle SLO unit 296 will be described below.

The light emitted from a light source 201-2 is led to the subject eye E as an observation target (inspection target) via lenses 235-11 to 235-12, an XY scanner 219-2, and a dichroic mirror 270-1.

The periphery of the light source 201-2 will be described below.

The light source 201-2 is an SLD similar to the light source 201-1 of the adaptive optics SLO unit 295. The wavelength of the light emitted from the light source 201-2 is about 910 nanometers, and the bandwidth thereof is about 10 nanometers. In this case, a wavelength of the light source 201-1 and a wavelength of the light source 201-2 are differentiated in order to separate the optical path of the adaptive optics SLO unit 295 and that of the wide viewing angle SLO unit 296 by using the dichroic mirror 270-1.

The optical path of measurement light 206-2 will be described below.

The measurement light 206-2 emitted from the light source 201-2 is led to the subject eye E as an observation target (inspection target) via a lens 235-2, the XY scanner 219-2, and the dichroic mirror 270-1. An X scanner, a component of the XY scanner 219-2, scans with the measurement light 206-2 in the direction parallel to paper. In the present case, a resonant scanner is used as the X scanner. The drive frequency of the X scanner is about 3.9 kHz. A Y scanner, a component of the XY scanner 219-2, scans with the measurement light 206-2 in the direction perpendicular to paper. In the present case, a Galvano scanner is used as the Y scanner. The drive waveform of the Y scanner is a sawtooth form of which the drive frequency is about 32 Hz and the duty ratio is about 81%. The drive frequency of the Y scanner is an important parameter which determines the frame rate of the above-described wide viewing angle image to be captured by the wide viewing angle SLO unit 296. The XY scanner 219-2 is controlled by the information processing apparatus 100 via an optical scanner driver 286 in the driver unit 280.

Although the beam diameter of the measurement light 206-2 is about 1 millimeter in this case, the beam diameter may be increased to acquire higher resolution images. When the measurement light 206-2 enters the subject eye E, the return light 208-2 produced by reflection and dispersion from the fundus Er reaches a light receiving unit 238-2 via the dichroic mirror 270-1, a lens 235-1, the XY scanner 219-2, and a beam splitter 258-2.

Apparatus Body Motor-Driven Stage Unit>>

The apparatus body motor-driven stage unit 297 illustrated in FIG. 3A will be described below.

The apparatus body motor-driven stage unit 297 is configured to move the adaptive optics SLO unit 295 and the wide viewing angle SLO unit 296 fixed to the apparatus body motor-driven stage unit 297, in the x, y, and z directions by using three different electric motors. The apparatus body motor-driven stage unit 297 is connected to an apparatus body motor-driven stage driver 285 in the driver unit 280. To perform alignment (i.e., positioning) on the subject eye E, the apparatus body motor-driven stage unit 297 is controlled by the information processing apparatus 100 via the apparatus body motor-driven stage driver 285.

<Hardware Configuration of Information Processing Apparatus>

A hardware configuration of the information processing apparatus 100 illustrated in FIG. 1A (and a hardware configuration of the information processing apparatus 100-1 illustrated in FIG. 2) will be described below.

Figure 4:
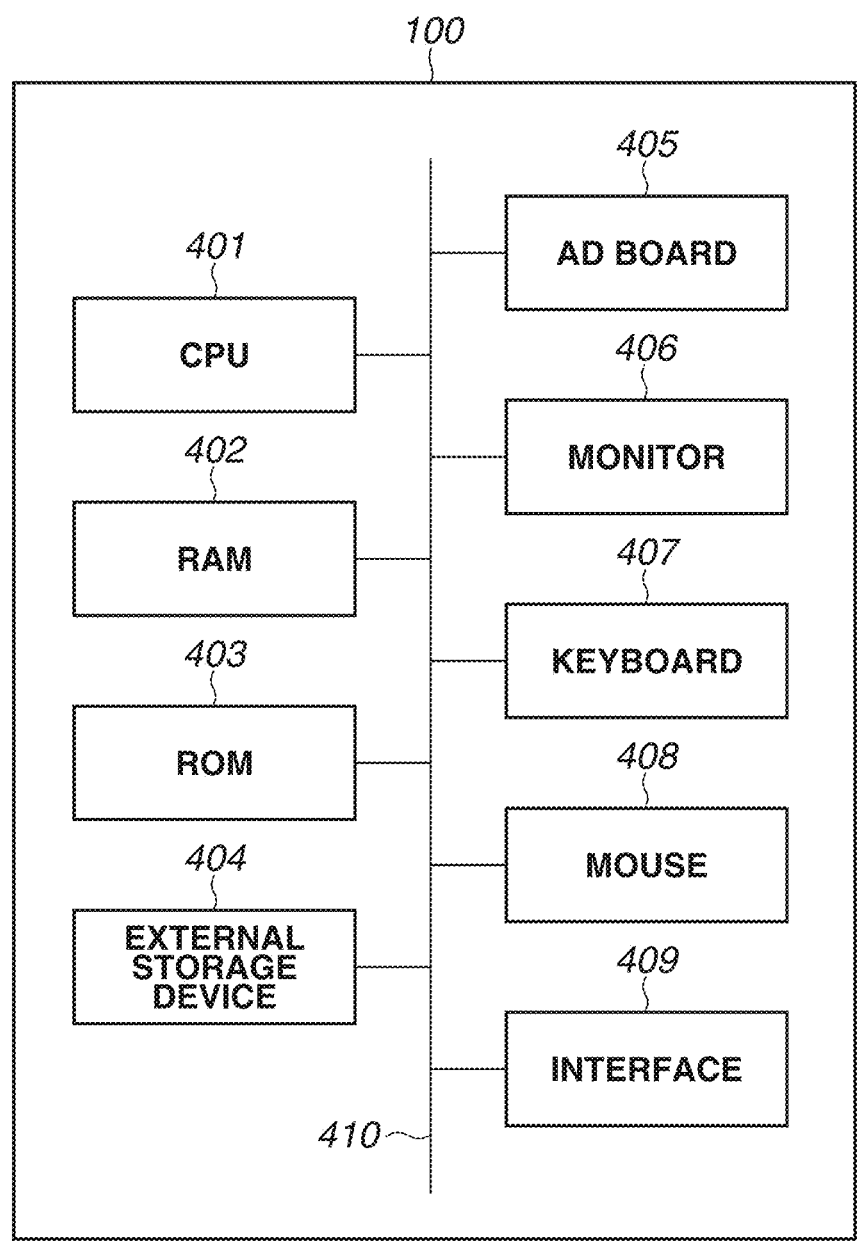
FIG. 4 is a block diagram illustrating an example of a hardware configuration of the information processing apparatus in FIGS. 1A and 1B according to exemplary embodiments of the present invention.

FIG. 4 is a block diagram illustrating an example of a hardware configuration of the information processing apparatus 100 illustrated in FIG. 1A according to exemplary embodiments of the present invention.

As illustrated in FIG. 4, the information processing apparatus 100 includes a central processing unit (CPU) 401, a random access memory (RAM) 402, a read only memory (ROM) 403, an external storage device 404, an AD board 405, a monitor 406, a keyboard 407, a mouse 408, an interface 409, and a bus 410.

The CPU 401 totally controls operations of the information processing apparatus 100 and performs various processing by using programs, data, and information stored in the ROM 403 or the external storage device 404.

The RAM 402 includes an area for temporarily storing a program and data loaded from the ROM 403 or the external storage device 404, and a work area required for the CPU 401 to perform various processing.

The ROM 403 stores programs, various types of data, and various types of information which do not need to be changed.

The external storage device 404 stores, for example, programs to be executed by an operating system (OS) and the CPU 401, and known data and information for the information processing apparatus 100. While, in the present exemplary embodiment, programs for performing processing according to the exemplary embodiments of the present invention are stored in the external storage device 404, storing the programs, for example, in the ROM 403 is also applicable to the present exemplary embodiment.

The AD board 405 performs processing for converting the voltage signals acquired by the light receiving units 238-1 and 238-2 illustrated in FIG. 3A into digital values.

The monitor 406 displays various types of images and various types of information, for example, under the control of the CPU 401.

The keyboard 407 and the mouse 408 are input devices provided for the information processing apparatus 100.

The interface 409 manages the transmission and reception of various types of information and various types of signals performed between the information processing apparatus 100 and external apparatuses (for example, the SLO image capturing apparatus 200, the data server 400, and the time phase data acquisition apparatus 500).

The bus 410 connects the CPU 401, the RAM 402, the ROM 403, the external storage device 404, the AD board 405, the monitor 406, the keyboard 407, the mouse 408, and the interface 409 to enable communication therebetween.

Programs for implementing the functions of the information processing apparatus 100 according to the present exemplary embodiment, and data used for executing the programs are stored in the external storage device 404. These programs and data are loaded into the RAM 402 via the bus 410 under the control of the CPU 401 and then executed by the CPU 401, as required.

The following describes an example of a correspondence relation between the hardware configuration of the information processing apparatus 100 illustrated in FIG. 4, and the functional configuration of the information processing apparatus 100-1 illustrated in FIG. 2.

For example, the data acquisition unit 110 illustrated in FIG. 2 is composed of the CPU 401, a program stored in the external storage device 404, and the interface 409 illustrated in FIG. 4. Further, for example, the storage unit 120 illustrated in FIG. 2 is composed of the RAM 402 illustrated in FIG. 4. Further, for example, the control unit 130 illustrated in FIG. 2 is composed of the CPU 401, a program stored in the external storage device 404, and the AD board 405 illustrated in FIG. 4. Further, for example, the instruction acquisition unit 140 illustrated in FIG. 2 is composed of the CPU 401, a program stored in the external storage device 404, the keyboard 407, and the mouse 408 or the interface 409 illustrated in FIG. 4. Further, for example, the display unit 150 illustrated in FIG. 2 is composed of the monitor 406 illustrated in FIG. 4.

(Information Processing Method by Information Processing Apparatus)

Figure 5A:
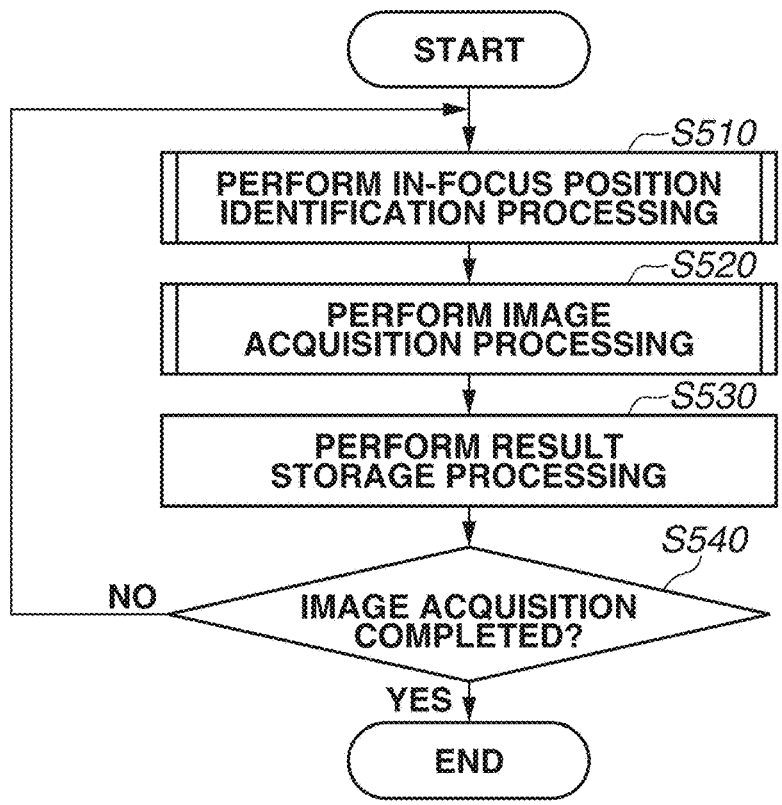
FIGS. 5A to 5C are flowcharts illustrating examples of processing in an information processing method performed by the information processing apparatus according to the first exemplary embodiment of the present invention.
Figure 5B:
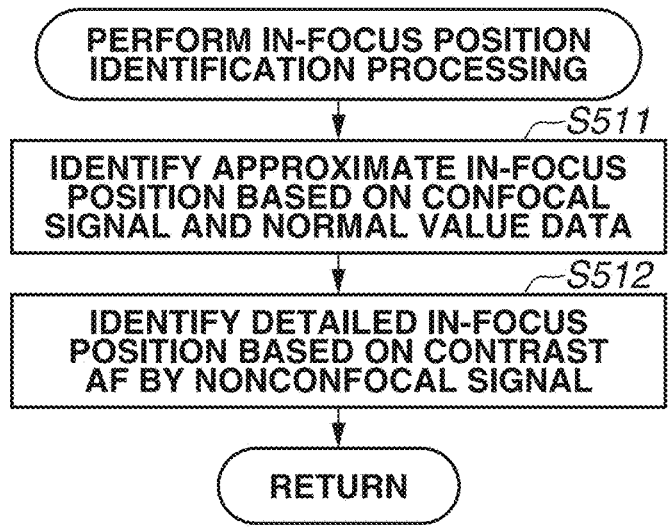
Figure 5C:
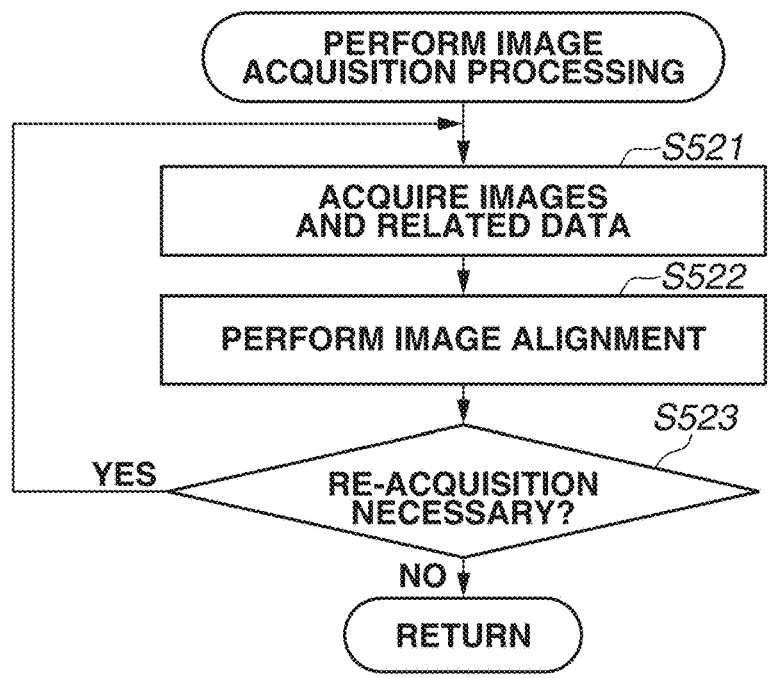

FIGS. 5A to 5C are flowcharts illustrating examples of processing in an information processing method performed by the information processing apparatus 100 according to the first exemplary embodiment of the present invention. The flowcharts illustrated in FIGS. 5A to 5C will be described below with reference to the functional configuration of the information processing apparatus 100-1 illustrated in FIG. 2.

<Step S510>

In step S510 illustrated in FIG. 5A, the aberration data acquisition unit 113 acquires aberration data detected by the wave front sensor 255. Then, the aberration compensation unit 131 compensates the aberration other than the defocus component of the Zernike polynomials, and instructs the motor-driven stage drive unit 133 to move the motor-driven stage 217, i.e., the focal lens 235-10, in the optical axis direction so that the defocus component becomes less than a predetermined value Td. In the vicinity of the macular region of the subject eye E, the reflective intensity at the boundary (IS/OS line) between the photoreceptor inner segment and the photoreceptor outer segment is high. Therefore, the vicinity of the IS/OS line is focused in the case of aberration compensation.

The in-focus position identification unit 132 identifies an approximate in-focus position for the retinal blood vessels of the subject eye E by adding normal value data related to a predetermined retina shape to an in-focus position (the position of the lens 235-10) obtained by using the confocal signal acquired by the confocal data acquisition unit 111 at the time of aberration compensation. More specifically, the in-focus position identification unit 132 identifies the approximate in-focus position for the retinal blood vessels of the subject eye E by adding normal value data related to the distance from the photoreceptor cell layer to the retina inner layers acquired from the data server 400 (or the storage unit 120) at the in-focus position focused through the aberration compensation processing. The in-focus position identification unit 132 further performs contrast automatic focusing processing based on the nonconfocal signal acquired by the nonconfocal data acquisition unit 112, and then identifies an accurate, detailed in-focus position for the retinal blood vessels of the subject eye E. Detailed processing in step S510 will be described below with reference to FIG. 5B.

<Step S520>

In step S520 illustrated in FIG. 5A, the data acquisition unit 110 (more specifically, the confocal data acquisition unit 111 and the nonconfocal data acquisition unit 112) acquire a confocal image and nonconfocal images at the in-focus position identified in step S510. Detailed processing in step S520 will be described below with reference to FIG. 5C.

<Step S530>

In step S530 illustrated in FIG. 5A, after the calculation unit 134 performs calculation between the nonconfocal images acquired in step S520, the display control unit 135 displays the acquired image and the image generated as a result of the calculation on the display unit 150.

Figure 6A:
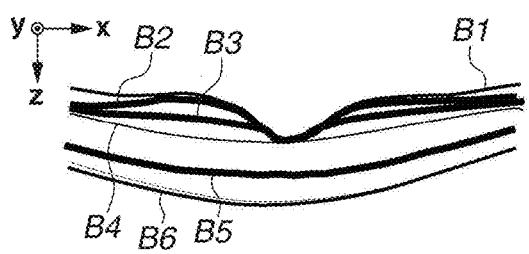
FIGS. 6A to 6L illustrate images of a subject eye for describing exemplary embodiments of the present invention.
Figure 6B:
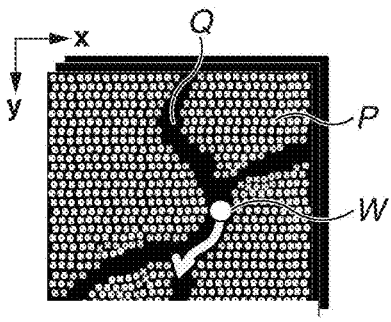
Figure 6C:
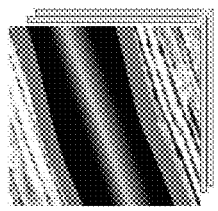
Figure 6D:
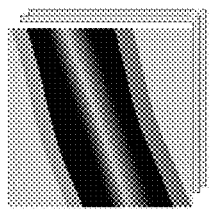
Figure 6E:
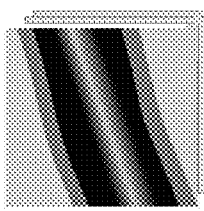
Figure 6F:
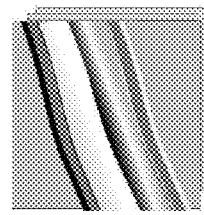

In the present exemplary embodiment, the calculation unit 134 generates the following images as nonconfocal images.
i) Addition averaging image of the R channel image Dnr and the L channel image Dnl ((Dnr+Dnl)/2 illustrated in FIG. 6E)
ii) Split detector image ((Dnl−Dnr)/(Dnr+Dnl) illustrated in FIG. 6F)
When generating a superposed image in i) and ii) described above, to eliminate effects of change in vessel diameter by the heartbeat, the control unit 130 selects only frames corresponding to pulse wave signals having a phase in a predetermined range out of frames of various types of moving images acquired and generated. The control unit 130 performs control to store focal and nonconfocal images acquired and generated in steps S520 and S530, for example, in the data server 400 (or the storage unit 120).

<Step S540>

In step S540 illustrated in FIG. 5A, for example, based on an instruction acquired by the instruction acquisition unit 140, the control unit 130 determines whether image acquisition in the present inspection is completed. When image acquisition in the present inspection is not completed (No in step S540), then the processing returns to step S510, and the control unit 130 performs processing in step S510 and subsequent steps.

On the other hand, when image acquisition in the present inspection is completed (YES in step S540), the processing exits the flowchart illustrated in FIG. 5A.

<Detailed Processing in Step S510>

Detailed processing in step S510 illustrated in FIG. 5A will be described below. FIG. 5B is a flowchart illustrating an example of detailed processing in step S510 in FIG. 5A.

<<Step S511>>

Figure 6G:
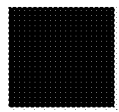
Figure 6H:
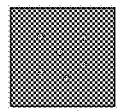
Figure 6I:
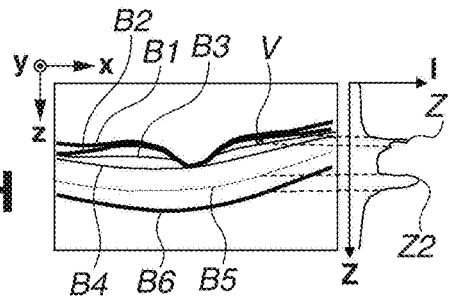

In step S511 illustrated in FIG. 5B, the in-focus position identification unit 132 identifies an approximate in-focus position for the retinal blood vessels of the subject eye E, by adding normal value data related to the distance between the photoreceptor cell layers B5 to B6 illustrated in FIG. 6I and the nerve fiber layers B1 to B2 illustrated in FIG. 6I, to the in-focus position focused by using a confocal signal at the time of aberration compensation. Although suitable normal value data for the relevant acquisition position is 150 micrometers, the value may change within a range from around 100 to 200 micrometers depending on the position on the fundus Er of the subject eye E, and may be set to an arbitrary value.

<<Step S512>>

In step S512 illustrated in FIG. 5B, the in-focus position identification unit 132 acquires the nonconfocal image Dn while changing the in-focus position in a predetermined range in the optical axis direction centering around the approximate in-focus position for the retinal blood vessels identified in step S511. While methods for changing the in-focus position include a method for moving the focal lens 235-10 and a method for changing the offset value of the defocus component to be given to the aberration compensation unit 131, in this case, the in-focus position will be changed by using the aberration compensation unit 131. Then, the in-focus position identification unit 132 performs the contrast automatic focusing processing based on the acquired nonconfocal image Dn, and then identifies an accurate, detailed in-focus position for the retinal blood vessels. In the present exemplary embodiment, the in-focus position identification unit 132 calculates the contrast of the nonconfocal image Dn acquired at each depth position of the subject eye E, and takes the depth position where the contrast value is maximized as an accurate, detailed in-focus position for the retinal blood vessels.

In the present exemplary embodiment, by using the addition average image ((Dnr+Dnl)/2) of the R channel image Dnr and the L channel image Dnl as a nonconfocal image Dn, the in-focus position identification unit 132 calculates the contrast in the nonconfocal image Dn. However, an arbitrary formula can be used to calculate the contrast. Although, in the present exemplary embodiment, the contrast is calculated by (maximum luminance value−minimum luminance value)/(minimum luminance value+maximum luminance value), the formula is not limited thereto and may be, for example, (maximum luminance value/minimum luminance value). Types of nonconfocal images and the evaluation value related to focusing are not limited thereto, and may be an arbitrary known image and evaluation value. For example, it is also possible to generate a split detector image ((Dnl−Dnr)/(Dnr+Dnl)) as a nonconfocal image, and identify the depth position in the split detector image where the edge intensity is maximum, as an in-focus position for the retinal blood vessels.

<Detailed Processing in Step S520>

Detailed processing in step S520 illustrated in FIG. 5A will be described below.

FIG. 5C is a flowchart illustrating an example of detailed processing in step S520 in FIG. 5A.

<<Step S521>>

In step S521 illustrated in FIG. 5C, based on the in-focus position for the retinal blood vessels identified in step S510, the data acquisition unit 110 acquires at least the nonconfocal images Dnk in the nonconfocal data acquisition unit 112, and acquires pulse data in the pulse data acquisition unit 114. More specifically, in the present exemplary embodiment, the data acquisition unit 110 acquires the wide viewing angle image Dl, the confocal images Dcj, the nonconfocal images Dnr and Dnl, and pulse data.

In more detail, the data acquisition unit 110 requests the SLO image capturing apparatus 200 to acquire the wide viewing angle image Dl, the confocal images Dcj, the nonconfocal images Dnrk and Dnlk, and the corresponding fixation target positions Fl and Fcn. In response to the acquisition request, the SLO image capturing apparatus 200 acquires the wide viewing angle image Dl, the confocal images Dcj, the nonconfocal images Dnrk and Dnlk, and the corresponding fixation target positions Fl and Fcn, and transmits such information to the information processing apparatus 100. The data acquisition unit 110 receives the wide viewing angle image Dl, the confocal images Dcj, the nonconfocal images Dnrk and Dnlk, and the fixation target positions Fl and Fcn from the SLO image capturing apparatus 200 via the LAN 300, and stores the information in the storage unit 120. In addition, the pulse data acquisition unit 114 requests the pulse data acquisition apparatus 500 to acquire the pulse data Pi related to biological signals. In the present exemplary embodiment, a pulse wave meter is employed as the pulse data acquisition apparatus 500 to acquire pulse wave data from the subject's earlobe as the pulse data Pi. The pulse wave data is represented as a point sequence having the acquisition time on one axis and the pulse wave signal value measured by the pulse wave meter on the other axis. In response to the acquisition request, the pulse data acquisition apparatus 500 acquires the corresponding pulse data Pi and then transmits it to the information processing apparatus 100. Therefore, the pulse data acquisition unit 114 receives the pulse data Pi from the pulse data acquisition apparatus 500 via the LAN 300. Then, the pulse data acquisition unit 114 stores the received pulse data Pi in the storage unit 120.

There are two possible cases of image acquisition timing. In one case, the confocal data acquisition unit 111 or the nonconfocal data acquisition unit 112 starts the image acquisition in synchronization with the phase having the pulse data Pi acquired by the pulse data acquisition apparatus 500. In the other case, the confocal data acquisition unit 111 and the nonconfocal data acquisition unit 112 simultaneously start the acquisition of the pulse data Pi and the image acquisition immediately after issuing an image acquisition request. In the present exemplary embodiment, the confocal data acquisition unit 111 and the nonconfocal data acquisition unit 112 start the acquisition of the pulse data Pi and the image acquisition immediately after issuing an image acquisition request. In this case, the pulse data acquisition unit 114 acquires the pulse data Pi of each image, detects external values of each pulse data Pi, and calculates the heartbeat cycle and the relative cardiac cycle. The relative cardiac cycle refers to a relative value represented by a floating point number from 0 to 1 when the period of the heart beat is 1.

FIG. 6C illustrates an example of a confocal image Dc when an image of the retinal blood vessels is captured, and FIG. 6D illustrates an example of a nonconfocal image Dnr when an image of the retinal blood vessels is captured. In the confocal image Dc illustrated in FIG. 6C, the background nerve fiber layer causes intense reflection, and alignment is likely to become difficult because of noise of the background portion. The nonconfocal image Dnr (R channel image) provides high contrast of the blood vessel wall on the right-hand side. On the other hand, the nonconfocal image Dnl (L channel image) provides high contrast of the blood vessel wall on the left-hand side.

<<Step S522>>

In step S522 illustrated in FIG. 5C, the control unit 130 performs inter-frame alignment for the acquired images. Subsequently, the control unit 130 determines exception frames based on the luminance value of each frame, noise, and the amount of displacement between each frame and a reference frame.

More specifically, the control unit 130 performs the inter-frame alignment in the wide viewing angle image Dl and the nonconfocal image Dnr, and applies inter-frame alignment parameter values to the nonconfocal image Dnl and the confocal images Dcj. The order of application of the inter-frame alignment parameter values between different image types is not limited thereto. For example, the inter-frame alignment parameter values calculated for the nonconfocal image Dnl may be applied to the nonconfocal image Dnr and the confocal images Dcj, and inter-frame alignment parameter values calculated for the confocal images Dcj may be applied to the nonconfocal images Dnr and Dnl.

Specific inter-frame alignment methods will be described below.

i) The control unit 130 sets a reference frame to be used as an alignment reference. In the present exemplary embodiment, a frame having the smallest frame number is used as a reference frame. The method for setting a reference frame is not limited thereto, and an arbitrary setting method may be used.

ii) The control unit 130 roughly associates inter-frame positions (coarse alignment). Although, an arbitrary alignment technique can be used, the control unit 130 according to the present exemplary embodiment performs coarse alignment by using correlation coefficients as inter-image similarity evaluation functions and the Affine conversion as a coordinate conversion technique.

iii) The control unit 130 performs fine alignment based on data of correspondence relation for inter-frame approximate positions.

The control unit 130 according to the present exemplary embodiment performs fine inter-frame alignment on the roughly aligned moving image acquired by the above-described method ii) by using the Free Form Deformation (FFD) method which is a type of nonrigid body alignment technique. The fine alignment technique is not limited thereto, and an arbitrary alignment technique may be used.

Subsequently, the control unit 130 performs alignment between the wide viewing angle image Dl and the high-magnification confocal images Dcj, and acquires relative positions of the high-magnification confocal images Dcj on the wide viewing angle image Dl. The control unit 130 further acquires the fixation target position Fcn used when capturing the high-magnification confocal images Dcj from the storage unit 120, and sets the acquired position as an initial point for searching for alignment parameters used in alignment between the wide viewing angle image Dl and the high-magnification confocal images Dcj. Then, the control unit 130 performs alignment between the wide viewing angle image Dl and the high-magnification confocal images Dcj while changing the combination of the parameter values. The control unit 130 further determines a combination of alignment parameter values having the highest similarity between the wide viewing angle image Dl and the high-magnification confocal images Dcj as a position of the high-magnification confocal images Dcj relative to the wide viewing angle image Dl. The alignment technique is not limited thereto, and an arbitrary alignment technique may be used.

When an intermediate-magnification image has been acquired in step S521, the control unit 130 sequentially performs alignment in ascending order of magnification. For example, when the high-magnification confocal image Dc1$m$ and the intermediate-magnification confocal image Dc2$o$ have been acquired, the control unit 130 performs alignment between the wide viewing angle image Dl and the intermediate-magnification confocal image Dc2$o$, and then performs alignment between the intermediate-magnification confocal image Dc2$o$ and the high-magnification confocal image Dc1$m$.

Further, the control unit 130 applies image pasting parameter values determined for the wide viewing angle image Dl and the high-magnification confocal images Dcj also to pasting of the nonconfocal images Dnrk and Dnlk. Thus, the relative positions of the high-magnification nonconfocal images Dnrk and Dnlk on the wide viewing angle image Dl are determined respectively.

<<Step S523>>

In step S523 illustrated in FIG. 5C, the control unit 130 determines whether image re-acquisition is required.

When any one of the following conditions is satisfied for each frame of the acquired moving image, the control unit 130 determines the relevant frame to be an exception frame.

a) When the amount of translational movement with respect to the reference frame of the moving image is a threshold value Ttr or larger b) When the average luminance value of each frame is less than a threshold value Tfi c) When the S/N ratio of each frame is less than a threshold value Tsn When observing an image as a moving image, it is desirable to continuously observe it as long as possible without exception frames inserted. In addition, when generating a superposed image, a fixed number of superimposable images are required. Therefore, in the present exemplary embodiment, when the maximum value of the interval between exception frame occurrences in each a moving image is less than a threshold value Te, or when the total number of normal frames is less than a threshold value Ts, the control unit 130 determines that re-acquisition of the relevant image is necessary. The method for determining whether image re-acquisition is not limited thereto, and an arbitrary known determination method may be used.

When re-acquisition of the relevant image is determined to be necessary (YES in step S523), the control unit 130 requests re-acquisition of the image from the data acquisition unit 110. Then, the processing returns to step S521.

On the other hand, when re-acquisition of the relevant image is determined to be not necessary (NO in step S523), the control unit 130 ends the processing in step S520 illustrated FIG. 5A. Then, the processing proceeds to step S530 illustrated in FIG. 5A.

Although, in the present exemplary embodiment, the retinal blood vessels of the subject eye E (more specifically, the blood vessel in the retina inner layers of the subject eye E) is an imaging target, the present invention is not limited thereto. For example, the present invention also includes a mode in which the capillary vessel in the retina of the subject eye E is an imaging target.

The information processing apparatus 100 according to the present exemplary embodiment identifies an approximate in-focus position by adding normal value data related to a predetermined retina shape to an in-focus position focused by using a confocal signal at the time of aberration compensation, and then identifies an accurate, detailed in-focus position for the retinal blood vessels of the subject eye E based on a nonconfocal signal. This configuration makes it possible to focus on the retinal blood vessels of the subject eye E in a robust and highly accurate way.

An information processing apparatus according to a second exemplary embodiment performs the following processing by using an apparatus for simultaneously acquiring a confocal signal and a nonconfocal signal of the subject eye E. More specifically, the information processing apparatus according to the present exemplary embodiment identifies an approximate in-focus position based on a peak position of the focal signal acquired while changing the in-focus position, and then identifies an accurate, detailed in-focus position by performing the contrast automatic focusing processing based at least on the nonconfocal signal.

More specifically, as illustrated in FIG. 3A, the SLO image capturing apparatus 200 for simultaneously acquiring the confocal images Dcj and the nonconfocal images Dnk obtains confocal images while changing the in-focus position at fixed intervals from the outer layer to the inner layer of the retina in the depth direction of the retina of the subject eye E. Then, the information processing apparatus calculates the average value (average luminance value) of the acquired confocal images. Then, the information processing apparatus selects in descending order a predetermined number of local maximum values of the average luminance values calculated at respective depth positions, and then identifies the depth position corresponding to the local maximum value in the retina innermost layer side as an approximate in-focus position for the retinal blood vessels. The following describes a case where the information processing apparatus identifies an in-focus position for the retinal blood vessels by performing the contrast automatic focusing processing on nonconfocal images acquired at depth positions within a predetermined range centering around the approximate in-focus position.

The overall configuration of an information processing system according to the second exemplary embodiment is similar to the overall configuration of the information processing system 10-1 according to the first exemplary embodiment illustrated in FIG. 1A, and descriptions thereof will be omitted. The functional configuration of an information processing apparatus according to the second exemplary embodiment is similar to the functional configuration of the information processing apparatus 100-1 according to the first exemplary embodiment illustrated in FIG. 2, and descriptions thereof will be omitted. The overall configuration of an SLO image capturing apparatus according to the second exemplary embodiment is similar to the overall configuration of the SLO image capturing apparatus 200 according to the first exemplary embodiment illustrated in FIG. 3A, and descriptions thereof will be omitted. The overall configuration of a light receiving unit 238-1 illustrated in FIG. 3A according to the second exemplary embodiment is similar to the overall configuration of the light receiving unit 238-1 according to the first exemplary embodiment illustrated in FIG. 3B, and descriptions thereof will be omitted. The hardware configuration of the information processing apparatus according to the second exemplary embodiment is similar to the hardware configuration of the information processing apparatus 100 illustrated in FIG. 4, descriptions thereof will be omitted. The following describes only portions different from the above-described first exemplary embodiment.

(Information Processing Method by Information Processing Apparatus)

The processing of the information processing method performed by the information processing apparatus 100 according to the second exemplary embodiment is basically similar to the processing of the information processing method performed by the information processing apparatus 100 according to the first exemplary embodiment illustrated in FIG. 5A. However, these two methods differ in detailed processing in step S510. The following describes the processing in step S510 of FIG. 5A by the information processing apparatus 100 according to the second exemplary embodiment.

<Step S510>

The in-focus position identification unit 132 instructs the confocal data acquisition unit 111 to acquire confocal images while moving the in-focus position in the depth direction, and the confocal data acquisition unit 111 acquires the confocal images. Subsequently, the in-focus position identification unit 132 calculates the average luminance value of the confocal images (frames) at each depth position, acquires in descending order a predetermined number of local maximum values of the average luminance values, and then identifies the depth position corresponding to the local maximum value in the retina innermost layer side as an approximate in-focus position for the retinal blood vessels. The in-focus position identification unit 132 further performs contrast automatic focusing processing based on the nonconfocal signal acquired in a predetermined depth range centering around the approximate in-focus position, and then identifies a detailed in-focus position for the retinal blood vessels. Detailed processing in step S510 illustrated in FIG. 5A according to the second exemplary embodiment will be described below.

<Detailed Processing in Step S510>

Figure 5D:
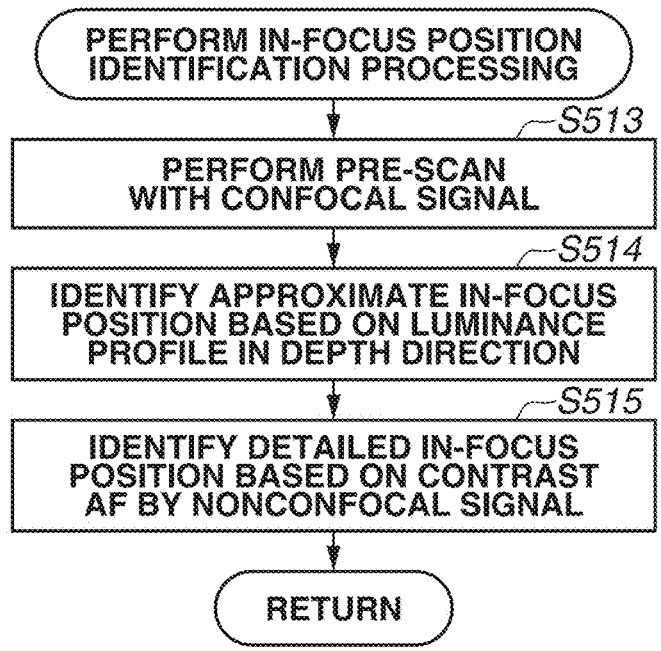
FIG. 5D is a flowchart illustrating an example of detailed processing in step S510 in FIG. 5A according to a second exemplary embodiment of the present invention.

FIG. 5D is a flowchart illustrating an example of detailed processing in step S510 illustrated in FIG. 5A according to the second exemplary embodiment of the present invention.

<<Step S513>>

In step S513 illustrated in FIG. 5D, the in-focus position identification unit 132 instructs the confocal data acquisition unit 111 to acquire confocal images while moving the in-focus position in the optical axis direction (depth direction). In response to the instruction, the confocal data acquisition unit 111 requests the SLO image capturing apparatus 200 to acquire confocal images at different positions in the depth direction. Then, the SLO image capturing apparatus 200 acquires confocal images according to the acquisition request, and transmits the images to the confocal data acquisition unit 111. The confocal data acquisition unit 111 stores the received confocal images in the storage unit 120. At this timing, the confocal data acquisition unit 111 acquires a confocal image at each position in the depth direction based on the acquisition request, and calculates the luminance average value. Imaging conditions for confocal images acquired here do not need to be identical to imaging conditions of target images.

In the present exemplary embodiment, the confocal images to be acquired for in-focus position identification have an identical imaging center position to an acquisition target image and a half viewing angle of the acquisition target image. The imaging conditions are not limited thereto. Confocal signals may be acquired by performing an arbitrary known scanning method at each depth position. For example, to identify an approximate in-focus position at higher speed, a confocal signal may be acquired at each depth position not through area scanning but through line scanning.

<<Step S514>>

In step S514 illustrated in FIG. 5D, the in-focus position identification unit 132 identifies an approximate in-focus position based on a luminance profile of confocal images (confocal signals) acquired at each position in the optical axis direction, i.e., in the depth direction of the retina.

More specifically, the in-focus position identification unit 132 calculates statistical values related to the luminance value of each confocal image, for example, the average luminance value of the confocal images, and generates a graph with one axis assigned to the average luminance value and the other axis assigned to the position in the depth direction (on the right-hand side in FIG. 6I). Then, the in-focus position identification unit 132 acquires a predetermined number of peak positions (two points Z1 and Z2 illustrated in FIG. 6I in the present exemplary embodiment) on the generated graph in descending order of the peak value, and takes the depth position equivalent to the peak position Z1 on the side of the retina inner layers as a depth position corresponding to the retinal nerve fiber layer. Then, the in-focus position identification unit 132 identifies the depth position as an approximate in-focus position for the retinal blood vessels.

Although, in the present exemplary embodiment, the in-focus position identification unit 132 identifies an approximate in-focus position at the peak position of the focal signals acquired at different depth positions, the present invention is not limited thereto. For example, the present invention also includes a case where the in-focus position specific parts 132 instructs the nonconfocal data acquisition unit 112 to acquire nonconfocal signals at different depth positions, and the in-focus position identification unit 132 identifies the depth position corresponding to the peak position on the retina inner layer side out of main peak positions of the acquired nonconfocal signals as an approximate in-focus position for the retinal blood vessels.

<<Step S515>>

In step S515 illustrated in FIG. 5D, the in-focus position identification unit 132 performs the contrast automatic focusing processing based on the acquired nonconfocal signals, and then identifies an accurate, detailed in-focus position for the retinal blood vessels. The specific contrast automatic focusing processing is similar to the above-described processing in step S512 according to the first exemplary embodiment, descriptions thereof will be omitted.

Although, in the present exemplary embodiment, the retinal blood vessels of the subject eye E (more specifically, blood vessels in the retina inner layers of the subject eye E) is an imaging target, the present invention is not limited thereto. For example, the present invention also includes a mode in which the capillary vessels in the retina of the subject eye E are an imaging target.

The information processing apparatus 100 according to the present exemplary embodiment identifies an approximate in-focus position for the retinal blood vessels based on the peak positions of the focal signals while changing the in-focus position, and then identifies an accurate, detailed in-focus position by performing the contrast automatic focusing processing based on the nonconfocal signal. This configuration makes it possible to focus on the retinal blood vessels of the subject eye E in a robust and highly accurate way.

An information processing apparatus according to a third exemplary embodiment stores the in-focus position identified at each image acquisition position when acquiring a confocal image and a nonconfocal image at different positions in the planar direction. The information processing apparatus further determines whether detailed focusing processing is necessary based on signal values acquired in approximate focusing processing. When the information processing apparatus determines that the detailed processing is necessary, it identifies the type of a signal to be used in the detailed focusing processing, and then identifies a detailed in-focus position by using the identified type of the signal.

More specifically, the information processing apparatus acquires confocal images at a plurality of imaging positions in the macular region, and then the control unit 130 determines whether the detailed focusing processing is necessary based on the size of the area of low-luminance regions occupying the relevant confocal images. When the information processing apparatus determines that the detailed focusing processing is necessary, it identifies the type of the signal to be used for the detailed focusing processing as a split detector image, a type of nonconfocal image, and then identifies a detailed in-focus position based on the identified type of the signal. Low-luminance regions in confocal images include the retina outer layers where the photoreceptor cells are lost. When acquiring confocal images for a region with a loss of the photoreceptor cells in a broad range, identifying a detailed in-focus position is difficult. On the other hand, the photoreceptor cells may be observed on nonconfocal images even in a case where the photoreceptor cells are lost in a broad range. Therefore, in case of a loss of the photoreceptor cells in a broad range, it is desirable to identify a detailed in-focus position based on nonconfocal images. Further, for an image acquisition position where the in-focus position identification is difficult even by using nonconfocal images, the information processing apparatus identifies an in-focus position by interpolating (or extrapolating) a stored in-focus position, i.e., an in-focus position at an image acquisition position adjacent to the image acquisition position.

This example will be described below.

(Overall Configuration of Information Processing System)

Figure 1B:
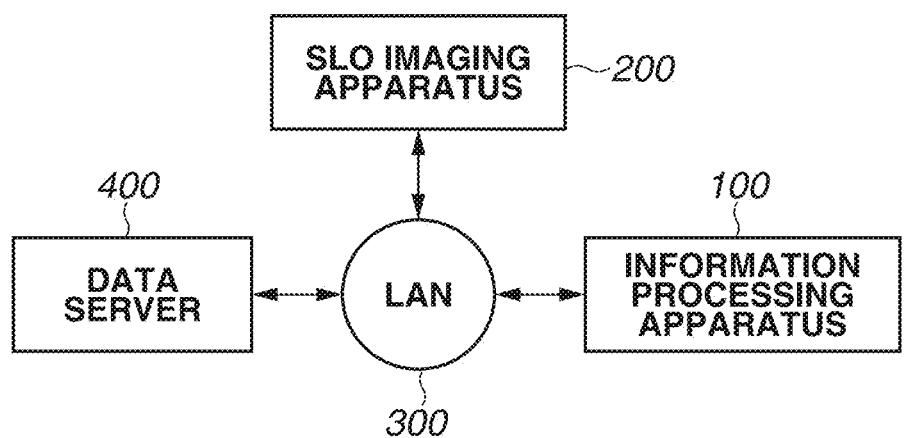
FIG. 1B illustrates an example of an overall configuration of an information processing system including an information processing apparatus according to a third exemplary embodiment of the present invention.

FIG. 1B illustrates an example of an overall configuration of an information processing system 10-3 including an information processing apparatus 100 according to the third exemplary embodiment of the present invention. As illustrated in FIG. 1B, the information processing system 10-3 includes the information processing apparatus 100, the SLO image capturing apparatus 200, the LAN 300, and the data server 400. In other words, the information processing systems 10-3 according to the third exemplary embodiment differ from the information processing system 10-1 according to the first exemplary embodiment illustrated in FIG. 1A in that the pulse data acquisition apparatus 500 is not included.

As illustrated in FIG. 1C, the information processing apparatus 100 is communicably connected with the SLO image capturing apparatus 200 or the data server 400 via the LAN 300.

The SLO image capturing apparatus 200 is apparatus for capturing the wide viewing angle image Dl, the confocal images Dcj, and the nonconfocal images Dnrk and Dnlk of the subject eye. The confocal images Dcj and the nonconfocal images Dnrk and Dnlk show higher magnifications than the wide viewing angle image Dl. The SLO image capturing apparatus 200 transmits the wide viewing angle image Dl, the confocal images Dcj, the nonconfocal images Dnrk and Dnlk, and information of the fixation target positions Fl and Fcn used for capturing these images, to the information processing apparatus 100 and the data server 400.

The data server 400 stores the wide viewing angle image Dl, the confocal images Dcj, and the nonconfocal images Dnrk and Dnlk of the subject eye, and image acquisition condition data such as the information about the fixation target positions Fl and Fcn used for capturing these images. In addition to these pieces of information, the data server 400 also stores image feature representing information of the subject eye. Although arbitrary information can be stored as the image feature representing information of the subject eye, the present exemplary embodiment handles information of a region where the photoreceptor cells are lost. The image feature representing information of the subject eye output by the information processing apparatus 100 is stored in the data server 400. In response to a request from the information processing apparatus 100, the data server 400 transmits the image feature representing information of the subject eye to the information processing apparatus 100.

The LAN 300 connects the information processing apparatus 100, the SLO image capturing apparatus 200, and the data server 400 to enable communication therebetween.

<Functional Configuration of Information Processing Apparatus>

FIG. 7 is a block diagram illustrating an example of a functional configuration of the information processing apparatus 100 illustrated in FIG. 1B according to the third exemplary embodiment of the present invention. Referring to FIG. 7, the information processing apparatus 100 according to the third exemplary embodiment is described as "the information processing apparatus 100-3." Referring to FIG. 7, elements identical to those in the configuration illustrated in FIG. 2 are assigned the same reference numeral.

As illustrated in FIG. 7, the information processing apparatus 100-3 includes the data acquisition unit 110, the storage unit 120, the control unit 130, the instruction acquisition unit 140, and the display unit 150.

The data acquisition unit 110 acquires various types of data, for example, from the SLO image capturing apparatus 200 and the data server 400 illustrated in FIG. 1B. As illustrated in FIG. 7, the data acquisition unit 110 includes the confocal data acquisition unit 111, the nonconfocal data acquisition unit 112, the aberration data acquisition unit 113, and an imaging condition data acquisition unit 115. The internal configuration of the data acquisition unit 110 will be described below, together with the flowcharts illustrated in FIGS. 8A and 8B.

The storage unit 120 stores various types of data and various types of information.

The control unit 130 totally controls operations of the information processing apparatus 100-3. As illustrated in FIG. 7, the control unit 130 includes the aberration compensation unit 131, the in-focus position identification unit 132, the motor-driven stage drive unit 133, the calculation unit 134, the display control unit 135, and a storage unit 136. The internal configuration of the control unit 130 will be described in detail below, together with the flowcharts illustrated in FIGS. 8A and 8B.

The instruction acquisition unit 140 acquires, for example, an instruction input from an inspector, and outputs it to the control unit 130.

The display unit 150 displays various types of images and various types of information under the control of the control unit 130 (more specifically, the display control unit 135).

The information processing apparatus 100-3 according to the third exemplary embodiment differs from the information processing apparatus 100-1 according to the first exemplary embodiment illustrated in FIG. 2 in that the data acquisition unit 110 includes the imaging condition data acquisition unit 115 instead of the pulse data acquisition unit 114, and that the storage unit 136 is added to the control unit 130.

The overall configuration of the SLO image capturing apparatus 200 according to the third exemplary embodiment is similar to the overall configuration of the SLO image capturing apparatus 200 according to the first exemplary embodiment illustrated in FIG. 3A, and descriptions thereof will be omitted. The overall configuration of the light receiving unit 238-1 illustrated in FIG. 3A according to the third exemplary embodiment is similar to the overall configuration of the light receiving unit 238-1 according to the first exemplary embodiment illustrated in FIG. 3B, and descriptions thereof will be omitted. The hardware configuration of the information processing apparatus 100 according to the third exemplary embodiment is similar to the hardware configuration of the information processing apparatus 100 illustrated in FIG. 4, and descriptions thereof will be omitted.

(Information Processing Method by Information Processing Apparatus)

Figure 8A:
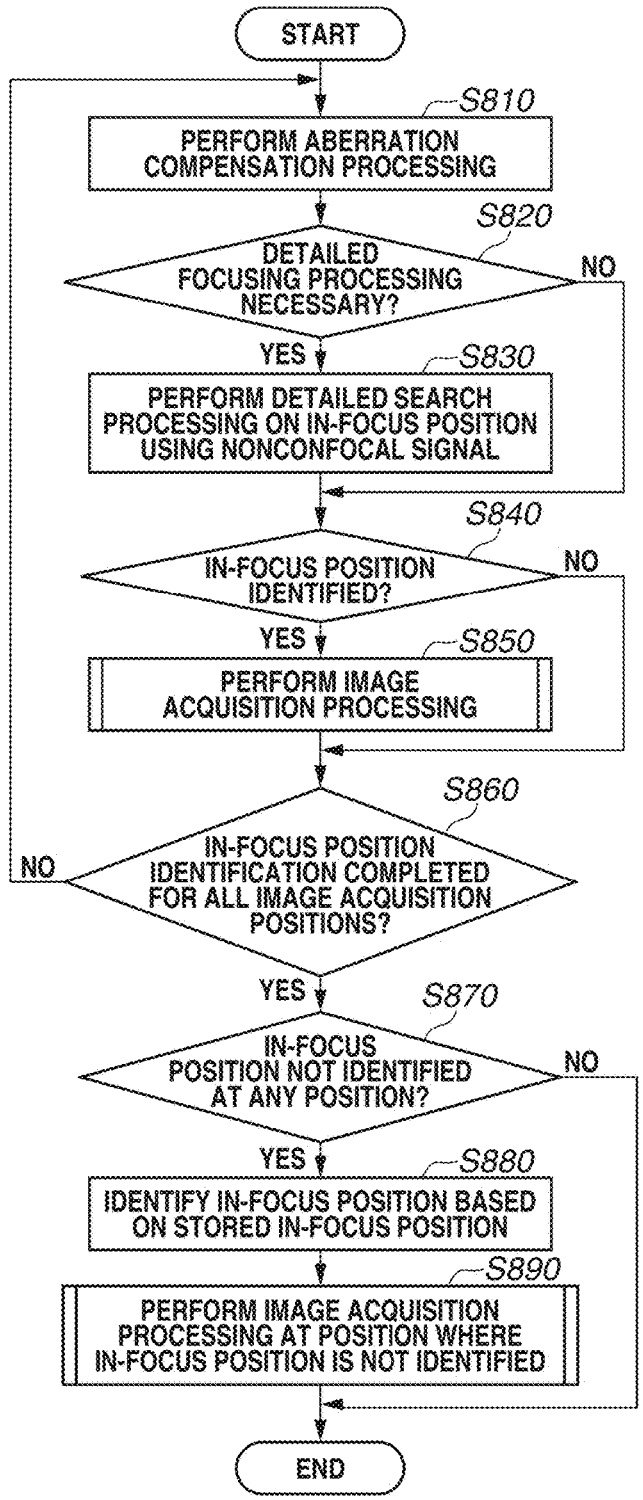
FIGS. 8A and 8B are flowcharts illustrating examples of processing of an information processing method performed by the information processing apparatus according to the third exemplary embodiment of the present invention.
Figure 8B:
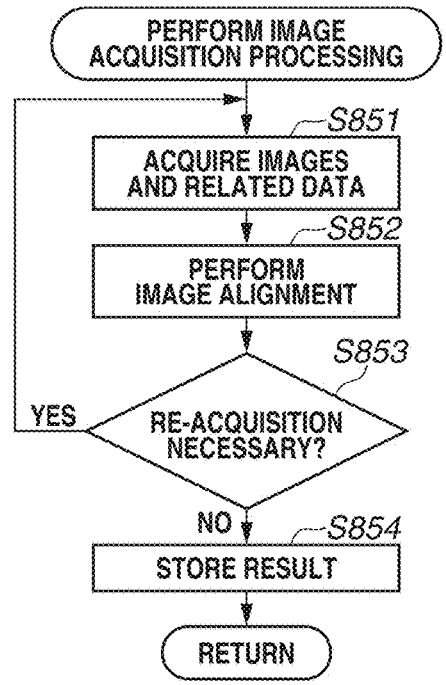

FIGS. 8A and 8B are flowcharts illustrating examples of processing in an information processing method performed by the information processing apparatus 100 according to the third exemplary embodiment of the present invention. The flowcharts illustrated in FIGS. 8A and 8B will be described below with reference to the functional configuration of the information processing apparatus 100-3 illustrated in FIG. 7.

<Step S810>

In step S810 illustrated in FIG. 8A, the aberration data acquisition unit 113 acquires aberration data detected by the wave front sensor 255. Then, the aberration compensation unit 131 compensates aberrations other than the defocus component of the Zernike polynomials. The control unit 130 instructs the motor-driven stage drive unit 133 to move the motor-driven stage 217 in the optical axis direction so that the defocus component becomes approximately 0. In response to the instruction, the motor-driven stage drive unit 133 moves the position of the focal lens 235-10 in the optical axis direction by the distance specified from the control unit 130 to make the defocus component approximately 0. Since reflection from the boundary between the photoreceptor inner segment and the photoreceptor outer segment is the highest in the macular region of the subject eye E, the in-focus position identification unit 132 will identify an approximate in-focus position for the photoreceptor cell layer based on the position of the focal lens 235-10 set by the processing in this step.

<Step S820>

In step S820 illustrated in FIG. 8A, the control unit 130 requests the confocal data acquisition unit 111 to acquire the confocal image at the image acquisition position (in the in-plane direction). In response to the instruction, the confocal data acquisition unit 111 acquires the confocal image from the SLO image capturing apparatus 200.

Generally, it is considered that the photoreceptor cells are first lost in the photoreceptor outer segment and then lost in the photoreceptor inner segment, and finally are killed.

According to the above-described Non-Patent Document 2, the confocal image Dc enables observation of the presence or absence of the photoreceptor outer segment, and the nonconfocal images Dnk enables observation of the presence or absence of the photoreceptor inner segment and the photoreceptor outer segment. Therefore, when an image of the visual cells with only the photoreceptor outer segment lost and retaining the healthy photoreceptor inner segment is captured, the photoreceptor cells are observed as a low-luminance region on the confocal image (see FIG. 6G), and the photoreceptor cells are observed on a split detector image which is a differential image of the nonconfocal image (see FIG. 6H).

Then, the control unit 130 refers to the luminance value on the confocal image at the relevant image acquisition position (in the in-plane direction). When an area of regions having the average luminance value less than Ti is less than Ta, the control unit 130 recognizes that the in-focus position for the photoreceptor cell layer has been identified. More specifically, in this case, the control unit 130 determines that it is not necessary to perform the detailed focusing processing on the confocal image (NO in step S820), and the processing proceeds to step S840.

On the other hand, when the control unit 130 refers to the luminance value on the confocal image at the relevant image acquisition position (in the in-plane direction) and an area of regions having the average luminance value less than Ti is equal to or larger than Ta, the control unit 130 determines that it is necessary to search for a detailed in-focus position by using a split detector signal, a type of a nonconfocal signal (YES in step S820), and the processing proceeds to step S830. In the present exemplary embodiment, the control unit 130 determines that it is necessary to search for an in-focus position by using a split detector signal only for an image acquisition position Dc5 out of nine image acquisition positions Dc1 to Dc9 illustrated in FIG. 6J.

<Step S830>

In step S830 illustrated in FIG. 8A, the in-focus position identification unit 132 performs the contrast automatic focusing processing based on nonconfocal images within a predetermined depth range centering around the approximate in-focus position acquired in step S810, and then identifies an accurate, detailed in-focus position for the photoreceptor cell layer. The specific contrast automatic focusing processing based on nonconfocal images is similar to the processing in step S512 illustrated in FIG. 5B according to the first exemplary embodiment, and descriptions thereof will be omitted.

<Step S840>

In step S840 illustrated in FIG. 8A, the in-focus position identification unit 132 determines whether an in-focus position has been identified. When the control unit 130 determines that it is not necessary to search for a detailed in-focus position (NO in step S820), the in-focus position identification unit 132 calculates the focusing degree of the confocal image and the nonconfocal image at the in-focus position acquired in step S810. On the other hand, when the control unit 130 determines that it is necessary to search for a detailed in-focus position (YES in step S820), the in-focus position identification unit 132 calculates the focusing degree of the confocal image and the nonconfocal image at the in-focus position acquired in step S830. In the present exemplary embodiment, the in-focus position identification unit 132 calculates the image contrast as the focusing degree. Although the contrast can be calculated by using an arbitrary formula, the present exemplary embodiment calculates the contrast by using a formula (maximum luminance value−minimum luminance value)/(minimum luminance value+maximum luminance value). However, the formula is not limited thereto. For example, a formula (maximum luminance value/minimum luminance value) may be used to calculate the contrast. The basis of the focusing degree is not limited to the image contrast. For example, an arbitrary known evaluation value, for example, the edge intensity may be set as the focusing degree.

When the focusing degree of a confocal image is equal to or larger than Tc or the focusing degree of a nonconfocal image is equal to or larger than Tn, the in-focus position identification unit 132 determines that an in-focus position has been identified. More specifically, in this case, the in-focus position identification unit 132 determines that an in-focus position has been identified (YES in step S840), and the storage unit 136 stores information about the in-plane position and the identified in-focus position in the storage unit 120. Then, the processing proceeds to step S850.

On the other hand, when the focusing degree of a confocal image is less than Tc and the focusing degree of a nonconfocal image is less than Tn, the in-focus position identification unit 132 determines that an in-focus position has not been identified. More specifically, in this case, the in-focus position identification unit 132 determines that an in-focus position has not been identified (NO in step S840), and the processing proceeds to step S860.

The method for determining whether an in-focus position has been identified is not limited thereto, and an arbitrary method may be used.

<Step S850>

In step S850 illustrated in FIG. 8A, the control unit 130 performs control to acquire the confocal images Dcj and the nonconfocal images Dnrk and Dnlk at the in-focus position identified by the in-focus position identification unit 132. Detailed processing in step S850 will be described below with reference to FIG. 8B.

<Step S860>

In step S860 illustrated in FIG. 8A, the control unit 130 determines whether in-focus position identification processing and image acquisition processing are completed at all of image acquisition positions predetermined in the inspection. When the control unit 130 determines that the in-focus position identification processing and the image acquisition processing are completed at not all of image acquisition positions predetermined in the inspection (NO in step S860), then in step S810, the control unit 130 performs processing in step S810 and subsequent steps for unprocessed image acquisition positions. On the other hand, when the control unit 130 determines that the in-focus position identification processing and the image acquisition processing are completed at all of image acquisition positions predetermined in the inspection (YES in step S860), the processing proceeds to step S870.

<Step S870>

In step S870 illustrated in FIG. 8A, the in-focus position identification unit 132 determines whether there is any position where an in-focus position has not been identified out of the image acquisition positions predetermined in the inspection. When the in-focus position identification unit 132 determines that there is no position where an in-focus position has not been identified out of the image acquisition positions predetermined in the inspection (NO in step S870), the processing exits the flowchart illustrated in FIG. 8A. On the other hand, when the in-focus position identification unit 132 determines that there is any position where an in-focus position has not been identified out of the image acquisition positions predetermined in the inspection (YES in step S870), the processing proceeds to step S880.
<Step S880>
In step S880 illustrated in FIG. 8A, with respect to an in-plane position where an in-focus position is determined to have not been identified in step S870, the control unit 130 acquires from the storage unit 120 information about the in-focus position identified at an image acquisition position adjacent to the in-plane position.

The method for acquiring the in-focus position information already acquired is not limited thereto. For example, the following method is also applicable. The imaging condition data acquisition unit 115 makes an inquiry to the data server 400 about the presence or absence of an in-focus position related to an acquired image in previous inspections for an identical subject. If the in-focus position exists, the imaging condition data acquisition unit 115 acquires information about the in-focus position of the acquired image at a closest inspection date and time from the data server 400, and then stores the information in the storage unit 120.

Then, the in-focus position identification unit 132 interpolates the acquired in-focus position at an adjacent position (or extrapolates the in-focus position when the storage unit 120 stores only the in-focus position on one side when viewed from an in-plane position where an in-focus position has not been identified), and then identifies an in-focus position at the in-plane position where an in-focus position has not been identified.

Figure 6J:
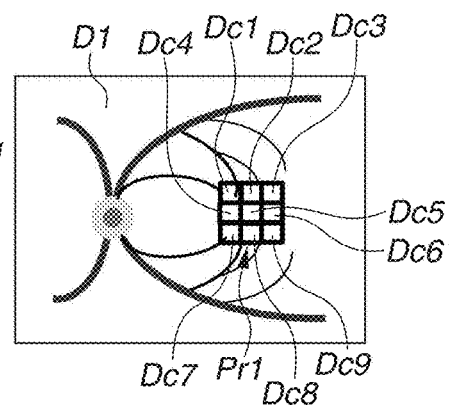

In the present exemplary embodiment, since an in-focus position has not been identified at the image acquisition position Dc5 illustrated in FIG. 6J, as described above, the in-focus position identification unit 132 identifies an in-focus position at the image acquisition position Dc5 by performing linear interpolation on in-focus positions at image acquisition positions Dc4 and Dc6 (or Dc2 and Dc8, or Dc1 and Dc9, or Dc3 and Dc7).

Figure 6K:
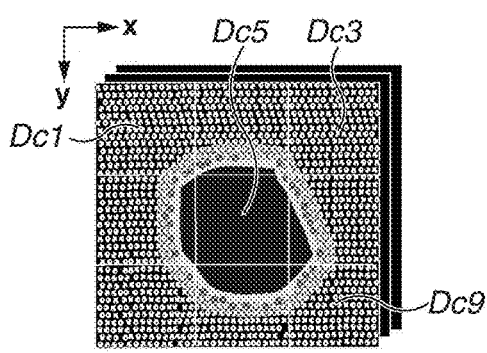
Figure 6L:
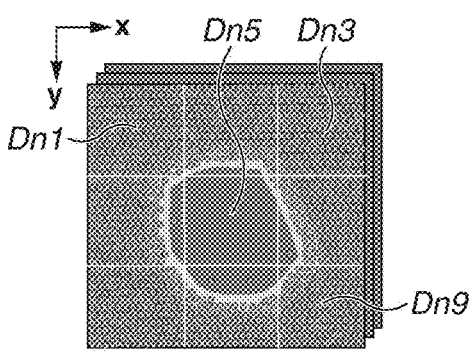

The method for identifying an in-plane position is not limited thereto. The in-focus position identification unit 132 may identify an in-focus position by using an arbitrary method as long as the method identifies an in-focus position by using an in-focus position at an adjacent in-plane position. For example, the in-focus position identification unit 132 may identify the in-focus position based on the average value of image acquisition positions Dc1, Dc2, Dc3, Dc4, Dc6, Dc7, Dc8, and Dc9 (or Dc2, Dc4, Dc6, and Dc8). Further, when the in-focus position at approximately the same position in previous inspections has been acquired, the in-focus position identification unit 132 may identify the in-focus position at approximately the same position in previous inspections as the in-focus position at the relevant position. In this case, for example, the present invention also includes a mode in which an in-focus position previously identified is prestored, and the in-focus position identification unit 132 identifies an approximate in-focus position of the subject eye E based on the stored in-focus position, and then identifies a detailed in-focus position of the subject eye E based on a nonconfocal signal.
<Step S890>
In step S890 illustrated in FIG. 8A, at an in-plane position where an in-focus position is determined to have not been identified in step S870, the control unit 130 acquires the confocal images Dcj and the nonconfocal images Dnrk and Dnlk by using the in-focus position identified in step S880. Detailed processing in step S890 will be described below with reference to FIG. 8B. Then, when the control unit 130 ends the processing in step S890, the processing exits the flowchart illustrated in FIG. 8A. The acquired confocal images Dc1 to Dc9 are illustrated in FIG. 6K, and the acquired nonconfocal images Dn1 to Dn9 are illustrated in FIG. 6L.
<Detailed Processing in Steps S850 and S890>
Detailed processing in steps S850 and S890 illustrated in FIG. 8A will be described below.

FIG. 8B is a flowchart illustrating an example of detailed processing in steps S850 and S890 illustrated in FIG. 8A.
<<Step S851>>
In step S851 illustrated in FIG. 8B, the data acquisition unit 110 acquires at least the confocal images Dcj and the nonconfocal images Dnk based on the in-focus position identified in step S810, S830, or S880. More specifically, in the present exemplary embodiment, the data acquisition unit 110 acquires the wide viewing angle image Dl, the confocal images Dcj, and the nonconfocal images Dnrk and Dnlk.
<<Step S852>>
In step S852 illustrated in FIG. 8B, the control unit 130 performs the inter-frame alignment on the acquired images. Subsequently, the control unit 130 determines exception frames based on the luminance value and the S/N ratio of each frame, and the amount of displacement between each frame and a reference frame. Subsequently, the control unit 130 performs alignment between the wide viewing angle image Dl and the confocal images Dcj, and acquires the relative positions of the confocal images Dcj on the wide viewing angle image Dl. Details of the specific inter-frame alignment and the image pasting processing are similar to the processing according to the first and the second exemplary embodiments, and descriptions thereof will be omitted.
<<Step S853>>
In step S853 illustrated in FIG. 8B, the control unit 130 determines whether image re-acquisition is necessary. Details of the processing for determining whether image re-acquisition are similar to the processing in step S523 illustrated in FIG. 5C according to the first exemplary embodiment, and descriptions thereof will be omitted.

When the control unit 130 determines that image re-acquisition is necessary (YES in step S853), the control unit 130 requests image re-acquisition from the data acquisition unit 110. Then, the processing returns to step S851.

On the other hand, when the control unit 130 determines that image re-acquisition is not necessary (NO in step S853), the processing proceeds to step S854.
<<Step S854>>
In step S854 illustrated in FIG. 8B, the storage unit 136 performs processing for associating information for identifying the inspection date and time and the subject eye E with the images acquired in step S851 and the images (the wide viewing angle image Dl, the confocal image Dc, and the nonconfocal images Dnr and Dnl) generated in step S852, and then storing these pieces of information. More specifically, the storage unit 136 performs processing for transmitting these pieces of information to the data server 400 to store these pieces of information in association with each other. The storage unit 136 further performs processing for storing information about the in-focus position identified at the time of each image acquisition in the storage unit 120, and at the same time performs processing for transmitting the information about the identified in-focus position to the data server 400.

In the present exemplary embodiment, based on the area of low-luminance regions in the confocal image acquired at the in-focus position which is identified at the time of aberration compensation by the control unit 130, the control unit 130 determines that the contrast automatic focusing processing based on the split detector signal, a type of a nonconfocal signal, is necessary, and then identifies a detailed in-focus position based on the split detector signal. However, the present invention is not limited thereto. For example, the control unit 103 acquires a confocal image and a nonconfocal image at an in-focus position identified at the time of aberration compensation, and performs the following processing depending on the value L of the linear sum of the focusing degrees calculated for the two images.

i) When L≥T2, the control unit 130 determines that the detailed focusing processing is not necessary (NO in step S820), then in step S840, the control unit 130 determines that an in-focus position has been identified at the in-focus position identified at the time of aberration compensation (YES in step S840), and the processing proceeds to step S850.

ii) When T1≤L<T2, the control unit 130 determines that the detailed focusing processing is necessary (YES in step S820), then in step S830, the control unit 130 searches for an in-focus position by using a nonconfocal signal.

iii) When L<T1, the control unit 130 determines that the detailed focusing processing is not necessary (NO in step S820), then in step S840, the control unit 130 determines that it is difficult to identify an in-focus position (NO in step S840), and the processing proceeds to step S860. (At the in-plane position, the control unit 130 identifies an in-focus position by interpolating an in-focus position at an adjacent acquisition position.)

Although, in the present exemplary embodiment, an approximate in-focus position is identified based on the confocal or nonconfocal signal at the image acquisition position, the present invention is not limited thereto. For example, the present invention also includes a case where, when the in-focus position at the image acquisition position adjacent to a target image acquisition position (in the in-plane direction) is stored in the storage unit 120, the control unit 130 identifies an in-focus position at the adjacent image acquisition position as an approximate in-focus position at the image acquisition position.

Although, in the present exemplary embodiment, the area of low-luminance regions in confocal images is used as a reference when determining whether the detailed focusing processing is necessary based on the signal value acquired at the time of the approximate focusing processing, an arbitrary known reference may be used as long as it is based on a signal value. For example, an image luminance statistical value (average value, median, minimum value, etc.) or the ratio of the area of low-luminance regions to the area of the entire image may be used as a reference.

The information processing apparatus 100 according to the present exemplary embodiment stores the in-focus position identified at each image acquisition position when acquiring a confocal image and a nonconfocal image at different positions in the planar direction. Then, the information processing apparatus 100 determines whether the detailed focusing processing is necessary based on the area of low-luminance regions in the confocal image. When the information processing apparatus 100 determines that the processing is necessary, it identifies the type of the signal to be used for the focusing processing as a nonconfocal image, and then identifies a detailed in-focus position by using the relevant type of the nonconfocal image. In the present case, low-luminance regions in a confocal image can be the retina outer layers where the photoreceptor cells are lost. For an image acquisition position where the in-focus position identification is difficult even by using a nonconfocal image, the information processing apparatus 100 identifies an in-focus position by interpolating (or extrapolating) the stored in-focus position, i.e., the in-focus position at the image acquisition position adjacent to the relevant image acquisition position.

This configuration makes it possible to focus on the retinal outer layers where low-luminance photoreceptor cells are lost on confocal images, in a robust and highly accurate way.

Although, in the above-described exemplary embodiments of the present invention, an in-focus position is identified by using an apparatus capable of acquiring a confocal image and a nonconfocal image at approximately the same time, the present invention is not limited thereto. For example, the present invention also includes a case where an in-focus position is identified, for example, by capturing the confocal image Dc through an SLO image capturing apparatus having an opening (pinhole) with a variable diameter and position provided before the optical sensor inside the light receiving unit 238-1, or by capturing the nonconfocal image Dn by moving a pinhole having a large diameter to the right or left of a retinal blood vessel current.

Although, in the above-described exemplary embodiments of the present invention, the type of the signal to be used for focusing processing is identified based on the value of the signal acquired by the data acquisition unit 110, the present invention is not limited thereto. For example, the type of the signal to be used for focusing processing may be identified based on the imaging region (the fundus position in the in-plane direction) of the signal acquired by the data acquisition unit 110. More specifically, since in the vicinity of the optic disk, an in-focus position is set to the retina inner layers immediately after the aberration compensation unit 131 completes the aberration compensation, nonconfocal images are used in the detailed in-focus position identification processing. On the other hand, since in the macular region, the retina outer layers are focused immediately after the aberration compensation unit 131 completes the aberration compensation, confocal images are used in the detailed in-focus position identification processing. Thus, the present invention also includes a case where the type of the signal to be used for focusing processing is identified in such a way. The present invention further includes a case where the type of the signal to be used for focusing processing is identified based on data related to the type of the signal to be used for focusing processing acquired via the instruction acquisition unit 140. Further, while, in the above-described exemplary embodiments of the present invention, the necessity of the detailed focusing processing is determined based on the value of the signal acquired by the data acquisition unit 110, the present invention is not limited thereto. For example, the present invention also includes a mode where the necessity of the detailed focusing processing is determined based on the above-described imaging region.

According to the above-described exemplary embodiments of the present invention, it becomes possible to focus on each imaging target of the subject eye E in a robust and highly accurate way.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2015-088679, filed Apr. 23, 2015, and No. 2015-250026, filed Dec. 22, 2015, which are hereby incorporated by reference herein in their entirety.

What is claimed is:

1. An information processing apparatus comprising:
   an acquisition unit configured to substantially simultaneously acquire a confocal signal and a nonconfocal signal based on return light from a subject eye irradiated with measurement light;
   an adjustment unit configured to adjust a position of a focusing member so as to move a focus of the measurement light in an optical axis direction of the measurement light by moving the focusing member; and
   an identification unit configured to identify an approximate position of the focusing member for focusing the measurement light to a retinal blood vessel based on the position of the focusing member adjusted by the adjustment unit using the confocal signal,
   wherein the adjustment unit adjusts the position of the focusing member for focusing the measurement light to the retinal blood vessel based on the approximate position and the nonconfocal signal.

2. The information processing apparatus according to claim 1, wherein the identification unit identifies the approximate position in a blood vessel in retina inner layers of the subject eye.

3. The information processing apparatus according to claim 1, wherein the identification unit controls the adjustment unit to adjust the position of the focusing member, by using the nonconfocal image, for focusing the measurement light to the retina outer layers of the subject eye where photoreceptor cells are lost.

4. The information processing apparatus according to claim 1, wherein the identification unit identifies the approximate position of the focusing member based on the confocal signal and normal value data of the subject eye.

5. The information processing apparatus according to claim 1, further comprising:
   a storage unit configured to store the position of the focusing member previously adjusted by the adjustment unit,
   wherein the identification unit identifies the approximate position of the focusing member based on the position stored in the storage unit.

6. The information processing apparatus according to claim 1, further comprising:
   an instruction unit configured to instruct a type of a signal to be used for focusing processing,
   wherein the identification unit controls the adjustment unit to adjust the position of the focusing member based on the signal of the type instructed by the instruction unit.

7. The information processing apparatus according to claim 1, wherein the acquisition unit acquires the confocal and the nonconfocal signals obtained by adjusting at least one of a position and a shape of an opening provided in the vicinity of an optical sensor for receiving the return light from the subject eye in an imaging apparatus for capturing an image of the subject eye.

8. An information processing method comprising:
   substantially simultaneously acquiring a confocal signal and a nonconfocal signal based on return light from a subject eye irradiated with measurement light;
   adjusting a focus position of the measurement light in an optical axis direction of the measurement light by moving a focusing member;
   identifying an approximate position of the focusing member for focusing the measurement light to a retinal blood vessel based on the position of the focusing member adjusted in the adjusting step using the confocal signal; and
   adjusting the position of the focusing member for focusing the measurement light to the retinal blood vessel based on the approximate position and the nonconfocal signal.

9. A non-transitory computer-readable recording medium storing a program for causing a computer to execute an information processing method, the information processing method comprising:
   substantially simultaneously acquiring a confocal signal and a nonconfocal signal based on return light from a subject eye irradiated with measurement light;
   adjusting a focus position of the measurement light in an optical axis direction of the measurement light by moving a focusing member;
   identifying an approximate position of the focusing member for focusing the measurement light to a retinal blood vessel based on the position of the focusing member adjusted in the adjusting step using the confocal signal; and
   adjusting the position of the focusing member for focusing the measurement light to the retinal blood vessel based on the approximate position and the nonconfocal signal.

* * * * *